US008048901B2

(12) United States Patent
Goerlitzer et al.

(10) Patent No.: US 8,048,901 B2
(45) Date of Patent: *Nov. 1, 2011

(54) 1,3-SUBSTITUTED CYCLOALKYL DERIVATIVES HAVING ACIDIC, MOSTLY HETEROCYCLIC GROUPS, PROCESSES FOR THEIR PREPARATION AND THEIR USE AS PHARMACEUTICALS

(75) Inventors: Jochen Goerlitzer, Frankfurt am Main (DE); Heiner Glombik, Hofheim (DE); Eugen Falk, Frankfurt (DE); Dirk Gretzke, Frankfurt (DE); Stefanie Keil, Hofheim (DE); Hans-Ludwig Schaefer, Hochheim (DE); Christian Stapper, Mainz (DE); Wolfgang Wendler, Selters (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 448 days.

This patent is subject to a terminal disclaimer.

(21) Appl. No.: 11/775,564

(22) Filed: Jul. 10, 2007

(65) Prior Publication Data
US 2008/0249126 A1 Oct. 9, 2008

Related U.S. Application Data

(63) Continuation of application No. 10/789,281, filed on Feb. 27, 2004, now abandoned.

(60) Provisional application No. 60/487,566, filed on Jul. 15, 2003.

(30) Foreign Application Priority Data

Feb. 27, 2003 (DE) .................. 103 08 351

(51) Int. Cl.
A61K 31/421 (2006.01)
C07D 263/34 (2006.01)
(52) U.S. Cl. ......... 514/374; 548/225; 548/235; 514/376
(58) Field of Classification Search .................. 548/225, 548/235; 514/374, 376
See application file for complete search history.

(56) References Cited

U.S. PATENT DOCUMENTS

| 3,174,901 | A | 3/1965 | Sterne |
| 5,190,923 | A | 3/1993 | Vincent et al. |
| 5,814,647 | A | 9/1998 | Urban et al. |
| 6,221,633 | B1 | 4/2001 | Ertl et al. |
| 6,221,897 | B1 | 4/2001 | Frick et al. |
| 6,245,744 | B1 | 6/2001 | Baringhaus et al. |
| 6,277,831 | B1 | 8/2001 | Frick et al. |
| 6,342,512 | B1 | 1/2002 | Kirsch et al. |
| 6,441,022 | B1 | 8/2002 | Baringhaus et al. |
| 6,506,778 | B2 | 1/2003 | Defossa et al. |
| 6,552,048 | B2 | 4/2003 | Kirsch et al. |
| 6,566,340 | B2 | 5/2003 | Frick et al. |
| 6,569,835 | B2 | 5/2003 | Frick et al. |
| 6,624,185 | B2 * | 9/2003 | Glombik et al. ............. 514/374 |
| 6,642,269 | B2 | 11/2003 | Frick et al. |
| 6,884,812 | B2 * | 4/2005 | Glombik et al. ............. 514/374 |
| 6,897,198 | B2 | 5/2005 | Baringhaus et al. |
| 7,148,246 | B2 | 12/2006 | Gretzke et al. |
| 7,399,777 | B2 | 7/2008 | Glombik et al. |
| 2004/0087648 | A1 | 5/2004 | Frick et al. |

FOREIGN PATENT DOCUMENTS

| EP | 0462884 A1 | 6/1991 |
| WO | WO 94/18183 | 8/1994 |
| WO | WO 94/18184 | 8/1994 |
| WO | WO 96/38428 | 12/1996 |
| WO | WO 97/26265 | 7/1997 |
| WO | 9728149 A1 | 8/1997 |
| WO | 9741097 A2 | 11/1997 |
| WO | WO 97/41097 | 11/1997 |
| WO | 9808871 A1 | 3/1998 |
| WO | WO 98/08871 | 3/1998 |
| WO | WO 98/19998 | 5/1998 |
| WO | 9903861 A1 | 1/1999 |
| WO | WO 99/03861 | 1/1999 |
| WO | 9915525 A1 | 4/1999 |
| WO | WO 99/15525 | 4/1999 |

(Continued)

OTHER PUBLICATIONS

Asakawa, A. et. al., Cocaine-Amphetamine-Regulated Transcript Influences Energy Metabolism Anxiety and Gastric Emptying in Mice, Hormone and Metabolic Reserch; vol. 33(9); 2001; pp. 554-558. Berger, J., et. al., The Mechanisms of Action of PPARs, Annul. Rev. Med.; vol. 53; 2002; pp. 409-435.
Fruchart, J.C., et. al., PPARs, Metabolic Disease and Atherosclerosis, Pharmacological Research; vol. 44, No. 5; 2001 pp. 345-352.
Kersten, S., et. al., Roles of PPARs in Health and Disease, Nature; vol. 405; May 25, 2000; pp. 421-424.

(Continued)

Primary Examiner — Joseph McKane
Assistant Examiner — Janet L Coppins
(74) Attorney, Agent, or Firm — Scully, Scott, Murphy & Presser, P.C.

(57) ABSTRACT

The invention relates to 1,3-substituted cycloalkyl derivatives having acidic, mostly heterocyclic groups and to their physiologically acceptable salts and physiologically functional derivatives.
What is described are compounds of the formula I,

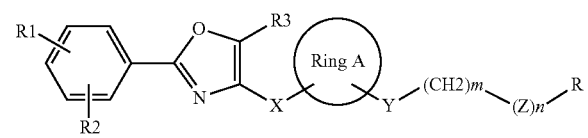

in which the radicals are as defined, and their physiologically acceptable salts and processes for their preparation. The compounds are suitable for the treatment and/or prevention of disorders of fatty acid metabolism and glucose utilization disorders as well as of disorders in which insulin resistance is involved.

26 Claims, No Drawings

FOREIGN PATENT DOCUMENTS

| | | |
|---|---|---|
| WO | WO 99/61431 | 12/1999 |
| WO | WO 99/62871 | 12/1999 |
| WO | WO 99/62872 | 12/1999 |
| WO | WO 99/67278 | 12/1999 |
| WO | WO 99/67279 | 12/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |
| WO | WO 01/21602 A1 | 3/2001 |
| WO | WO-01/21602 A1 * | 3/2001 |
| WO | WO 01/40169 A1 | 6/2001 |
| WO | WO 01/40171 A1 | 6/2001 |
| WO | WO 01/72290 A2 | 10/2001 |
| WO | WO 01/81327 A1 | 11/2001 |
| WO | WO 01/83451 | 11/2001 |
| WO | WO 01/85695 A1 | 11/2001 |
| WO | WO 01/91752 A1 | 12/2001 |
| WO | 0218355 A1 | 3/2002 |
| WO | WO 02/30895 | 4/2002 |
| WO | WO 02/38541 A1 | 5/2002 |
| WO | WO 02/50027 | 6/2002 |
| WO | WO 02/096864 | 12/2002 |
| WO | WO 02/100403 A1 | 12/2002 |
| WO | 03011819 A1 | 2/2003 |
| WO | WO 03/020269 | 3/2003 |
| WO | 03072102 A1 | 4/2003 |
| WO | WO 03/040174 | 5/2003 |
| WO | WO 03/043985 | 5/2003 |
| WO | WO 03/084922 | 10/2003 |
| WO | WO 03/084923 | 10/2003 |
| WO | WO 03/104188 | 12/2003 |

OTHER PUBLICATIONS

Kliewer, S.A., et. al., Peroxisome Proliferator-Activated Receptors: From Genes to Physiology, Recent Prog. Horm Res.; vol. 56; 2001; pp. 239-263.

Lee, D.W., et. al., Leptin agonists as a potential approach to the treatment of obesity, Drugs of the Future; vol. 26(9); 2001; pp. 873-881.

Motojima, K., et. al., Peroxisome Proliferator-Activated Receptor (PPAR): Structure, Mechanisms of Activation and Diverse Functions, Cell Structure and Function; vol. 18; 1993; pp. 267-277.

Okada, H., et. al., Synthesis and Antitumor Activities of Prodrugs of Benzoylphenylureas, Chem. Pharm. Bull.; vol. 42(1); 1994; pp. 57-61.

Pineda Torra, I., et. al., Peroxisome Proliferator-activated Receptors: from Transcriptional Control to Clinical Practice, Curr. Opin. Lipidol; vol. 12; 2001; pp. 245-254.

Pineda Torra, I., et. al., Peroxisome proliferator-activated receptor alpha in metabolic disease, inflammation, atherosclerosis and aging, Curr. Opin. Lipidol; vol. 10; 1999; pp. 151-159.

Vidal-Puig, A., et. al., Regulation of PPAR y Gene Expression by Nutrition and Obesity in Rodents, J. Clin. Invest.; vol. 97, No. 11, 1996; pp. 2553-2561.

Wilson, T.M., et. al., The PPARs: From Orphan Receptors to Drug Discovery, Journal of Medicinal Chemistry; vol. 43, No. 4; 2000; pp. 527-550.

Zunft, H.J.F., et. al., Carob Pulp Preparation for Treatment of Hypercholesterolemia, Advances in Natural Therapy; vol. 18, No. 5; Sep.-Oct. 2001; pp. 230-236.

Amri E. et al., "Cloning of a Protein That Mediates Transcriptional Effects of Fatty Acids in Preadipocytes", The Journal of Biological Chemistry, 270(5):2367-2371 (Feb. 1995).

Beck F. et al., "The ontogeny of perosisome-proliferator-activated receptor gene expression in the mouse and rat", Proc. R. Soc. Lond. B. 247:83-87 (1992).

Colville-Nash P. et al., "Inhibition of Inducible Nitric Oxide Synthase by Peroxisome Proliferator-Activated Receptor Agonists: Correlation with Induction of Heme Oxygenase 1", The Journal of Immunology, 161:978-984 (1998).

De Faire U. et al., "Retardation of Coronary Atherosclerosis: The Bezafibrate Coronary Atherosclerosis intervention Trial (BECAIT) and Other Angiographic Trials", Cardiovasc Drugs Ther, 11:257-263 (1997)..

Demetri G. et al., "Induction of solid tumor differentiation by the peroxisome proliferator-activated receptor-γ ligand troglitazone in patients with liposarcoma", Proc. Natl. Acad. Sci. USA, 96:3951-3956 (Mar. 1999).

Dunaif A. et al., "The Insulin-Sensitizing Agent Troglitazone Improves Metabolic and Reproductive Abnormalities in the Polycystic Ovary Snydrome", Journal of Clinical Endocrinology of Metabolism, 81(9):3299-3306 (1996).

Elbrecht A. et al., "Molecular Cloning, Expression and Characterization of Human Peroxisome Proliferator Activated Receptors γ1 and γ2", Biochemical arid Biophysical Research Communications, 224:431-437 (1996).

Elstner E. et al., "Ligands for peroxisome proliferator-activated receptor γ and retinoic acid receptor inhibit growth and induce apoptosis of human breast cancer cells in vitro and in BNX mice", Proc. Nati. Acad. Sci, USA, 95:8806-8811 (Jul. 1998).

Forman B. et al. "15-Deoxy-Delta 12, 14-Prostaglandin J2 is a Ligand for the Adipocyte Determination Factor PPARγ", Cell, 83:803-812 (Dec. 1, 1995).

Frick M. et al. "Prevention of the Angiographic Progression of Coronary and Vein-Graft Atherosclerosis by Gemifibrozil After Coronary Bypass Surgery in Men with Low Levels of HDL Cholesterol", Circulation, 96:2137-2134 91997).

Göttlicher M. et al., "Fatty acids activate a chimera of the clofibric acid-activated receptor and the glucocoritcoid receptor", Proc. Natl. Acad. Sci. USA, 89:4653-4657 (May 1992).

Green S. "Receptor-Mediated Mechanisms of Peroxisome Proliferators", Biochemical Pharmacology, 43(3):393-401 (1992).

Horikoshi H. et al., "Troglitazone—a novel antidiabetic drug for treating insulin resistance", DDT, 3(2):79-88 (Feb. 1998).

Lehmann J. et al., "An Antidiabetic Thiazolidinedione is a High Affinity Ligand for Peroxisome Proliferator-activated Receptor γ (PPARγ)", The Journal of Biological Chemtry, 270(22):12953-12956 (1995).

Löhrke B. et al., "Detection and functional characterisation of the transcription factor peroxisome proliferator-activated receptor γ in luetin cells", Journal of Endocrinology, 159:249-439 (1998).

Poynter M. et al., "Peroxisome Proliferator-activated Receptor α Activatoiri Modulatese Cellular Redox Status, Represses Nuclear Factor-κB Signaling, and Reduces Inflammatory Cytokine Production in Aging", The Journal of Biological Chemistry, 273(49):32833-23841 (1998).

Salvador J. et al., "Perspectives in the therapeutic use of leptin", Expert Opin. Pharmacother, 2(10):1615-1622 (2001).

Sarraf P. et al., "Differentiation and reversal of malignant changes in colon cancer through PPARγ," Nature Medicine, 4(9):1046-1052 (Sep. 1998).

Schmidt A. et al., "Identification of a New Member of the Steroid Hormone Receptor Superfamily That Is Activated by a Peroxisome Proliferator and Fatty Acids" Molecular Endocrinology, 6:1634-1641 (1992).

Schoonjas K. et al., "Peroxisome proliferator-activated receptors, orphans with ligands and functions" Current Opinion on Lipidology, 8:159-166 (1997).

Staels B. et al "Role of PPAR in the Pharmacologic Regulations of Lipoprotein Metabolism by Fibrates and Thiazolidinediones", Current Pharmaceutical Design, 3:1-14 (1997).

Staels B. et al., "Activation of human aortic smooth-muscle cells is inhibited by PPPARα but not by PPARγ activators", Nature, 393:790-793 (1998).

Tyle P., "Iontophoretic Devices for Drug Delivery", Pharmaceutical Research, 3(6):318-326 (1986).

* cited by examiner

1,3-SUBSTITUTED CYCLOALKYL DERIVATIVES HAVING ACIDIC, MOSTLY HETEROCYCLIC GROUPS, PROCESSES FOR THEIR PREPARATION AND THEIR USE AS PHARMACEUTICALS

The invention relates to 1,3-substituted cycloalkyl derivatives having acidic, mostly heterocyclic groups, and to their physiologically acceptable salts and physiologically functional derivatives.

Compounds of a similar structure have already been described in the prior art for the treatment of hyperlipidaemia and diabetes (WO 2000/64876).

The invention was based on the object of providing compounds which permit therapeutically utilizable modulation of lipid and/or carbohydrate metabolism and are thus suitable for the prevention and/or treatment of diseases such as type 2 diabetes and atherosclerosis and the diverse sequelae thereof.

A series of compounds which modulate the activity of PPA receptors has surprisingly been found. The compounds are suitable in particular for activating PPARalpha and PPAR-gamma, it being possible for the extent of the relative activation to vary depending on the compounds.

Accordingly, the invention relates to compounds of the formula I

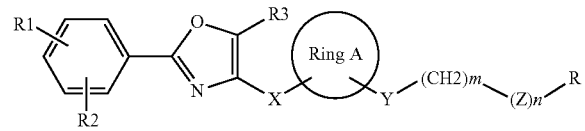

I wherein
ring A is $(C_3-C_8)$-cycloalkanediyl or $(C_3-C_8)$-cycloalkenediyl, wherein one or more carbon atoms in said $(C_3-C_8)$-cycloalkanediyl and $(C_3-C_8)$-cycloalkenediyl groups are optionally replaced by oxygen atoms;
R1, R2 are each independently H, F, Br, Cl, $SF_5$, S—$(C_1-C_6)$-alkyl, $CF_3$, $OCF_3$, $(C_1-C_6)$-alkyl, O—$(C_1-C_6)$-alkyl, $SCF_3$, phenoxy, $OCF_2CHF_2$, $OCF_2CF_3$, $(C_1-C_6)$-alkyl-$(C_1-C_6)$-alkoxy, O$(C_1-C_6)$-alkyl-$(C_1-C_6)$-alkoxy or benzyloxy;
R3 is H, $CF_3$, $(C_1-C_6)$-alkyl, $(C_3-C_8)$-cycloalkyl or phenyl;
X is $(C_1-C_6)$-alkanediyl, wherein one or more carbon atoms therein are optionally replaced by oxygen atoms;
Y is S, O or a bond;
m is 1, 2 or 3;
n is 0 or 1;
Z is O, S, CO or CO—NH;
R is H, OH, $CH_2$—CO—NH—OH, $CH_2$—CO—NH—$(C_1-C_6)$-alkyl, $CH_2$—CO—NH—$(C_1-C_6)$-alkoxy, NR4R5 or a 5-, 6-, 7-, 8-, 9-, 10-, 11- or 12-membered mono or bicyclic ring that is unsaturated, partially unsaturated or saturated, and optionally contains one to four heteroatoms selected from the group consisting of N, O and S, and wherein said 5-, 6-, 7-, 8-, 9-, 10-, 11- or 12-membered mono or bicyclic ring is optionally benzo-fused, and optionally substituted by F, Cl, Br, CN, SH, COOH, $(C_1C_4)$-alkyl, $(C_1-C_6)$-alkoxy, $SO_2$—$(C_1-C_4)$-alkyl, $NO_2$, $CF_3$, $OCF_3$, $(C_1-C_6)$-alkyl-$(C_1-C_6)$-alkoxy, $(C_1-C_6)$-alkoxy-$(C_1-C_6)$-alkoxy, $(C_1-C_6)$-alkoxy-phenyl, phenoxy, $NHSO_2CF_3$ or $B(OH)_2$;
R4 is H or $(C_1-C_6)$-alkyl;
R5 is OH, $NH_2$, $SO_2$—$CF_3$, $SO_2$-phenyl-$CF_3$, CO—$CF_3$, $(C_1-C_6)$-alkoxy or phenyl optionally substituted by $CH_3$ or COOH; or R4 and R5, taken together with the nitrogen atom to which they are attached, form a 5-membered aromatic heterocycle which is optionally fused to an aromatic 5-, 6-, or 7-membered ring, said aromatic 5-, 6-, or 7-membered ring optionally having one, two, three or four nitrogen atoms, and optionally substituted by F, Cl, Br, $CF_3$, $OCF_3$, COOH, $SO_2CH_3$, CN, $(C_1-C_4)$-alkoxy, $(C_1-C_4)$-alkyl, $(C_1-C_6)$-alkyl-phenyl, $(C_1-C_6)$-alkyl-$(C_1-C_6)$-alkoxy, $(C_1-C_6)$-alkoxy-$(C_1-C_6)$-alkoxy, $(C_1-C_6)$-alkoxy-phenyl or phenoxy;
and pharmaceutically acceptable salts thereof.

Preference is given to compounds of the formula I wherein ring A is $(C_3-C_8)$-cycloalkanediyl, wherein one carbon atom is optionally replaced by an oxygen atom; and
X is $(C_1-C_6)$-alkanediyl, wherein one carbon atom is optionally replaced by an oxygen atom.

Also preferred are compounds of the formula I wherein ring A is cyclohexane-1,3-diyl; and
X is $CH_2$—O.

Also preferred are compounds of the formula I wherein ring A is cyclohexane-1,3-diyl;
X is $CH_2$—O; and
Y is O.

Particular preference is given to compounds of the formula I in which the central cycloalkane-1,3-diyl ring is attached cis.

Particular preference is also given to compounds of formula I wherein:
R1/R2 are each independently H, $(C_1-C_4)$-alkyl or $(C_1-C_4)$-alkoxy; and
R3 is $(C_1-C_4)$-alkyl.

Particular preference is furthermore given to compounds of the formula I wherein:
Y is O;
m is 3; and
n is 0.

Also particularly preferred are compounds of the formula I wherein:
Y is O;
m is 2; and
n is 0.

Also particularly preferred are compounds of the formula I wherein:
Y is O;
m is 2;
n is 1; and
Z is O.

Also particularly preferred are compounds of the formula I wherein:
Y is O;
m is 1; and
n is 0.

Also particularly preferred are compounds of the formula I wherein:
Y is a bond;
m is 1; and
n is 0.

Also particularly preferred are compounds of the formula I wherein:
Y is a bond;
m is 1;
n is 1; and
Z is O.

Very particular preference is given to compounds of the formula I wherein:
Y is O;
m is 3;

n is 0; and
R is tetrazole or NHSO$_2$CF$_3$.

Also very particularly preferred are compounds of the formula I wherein:
Y is O;
m is 2;
n is 0; and
R is tetrazole, NHSO$_2$CF$_3$ or NR4R5 denoting indole or 6-azaindole and wherein said indole and 6-azaindole groups are optionally substituted by F, Br, CN, COOH, (C$_1$C$_4$)-alkyl, (C$_1$-C$_4$)-alkoxy, SO$_2$—CH$_3$, (C$_1$-C$_6$)-alkoxy-(C$_1$-C$_6$)-alkoxy or benzoxy.

Also very particularly preferred are compounds of the formula I wherein:
Y is O;
m is 2;
n is 1;
Z is O; and
R is phenyl or thiophene, each of which is optionally substituted by F, COOH, (C$_1$-C$_4$)-alkyl, (C$_1$-C$_4$)-alkoxy, NO$_2$, CF$_3$, benzyloxy or B(OH)$_2$.

Also very particularly preferred are compounds of the formula I wherein:
Y is O;
m is 1;
n is 0; and
R is phenyl optionally substituted with NHSO$_2$CF$_3$ or B(OH)$_2$.

Also very particularly preferred are compounds of the formula I wherein:
Y is a bond;
m is 1;
n is 0; and
R is NR4R5 denoting pyrrole or indole, both of which are substituted by COOH.

Also very particularly preferred are compounds of the formula I wherein:
Y is a bond;
m is 1;
n is 1;
Z is O; and
R is thiophene or benzothiophene, each of which is optionally substituted by COOH, Cl or CF$_3$.

This invention also encompasses all combinations of preferred aspects of the invention described herein.

The alkyl radicals in the substituents R, R1, R2, R3, R4 and R5 may be either straight-chain or branched.

Aryl means an aromatic carbocyclic mono- or bicyclic ring system which comprises 6 to 10 atoms in the ring or rings.

Heteroaryl is a mono- or bicyclic aromatic ring system having 4 to 11 ring members, in which at least one atom in the ring system is a heteroatom from the series N, O and S.

The compounds of the formula I comprise at least two centers of asymmetry and may comprise more in addition. The compounds of the formula I may therefore exist in the form of their racemates, racemic mixtures, pure enantiomers, diastereomers and mixtures of diastereomers. The present invention encompasses all these isomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 May 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Compounds of this type are particularly suitable for the treatment and/or prevention of 1.
   disorders of fatty acid metabolism and glucose utilization disorders
   disorders in which insulin resistance is involved
2. Diabetes mellitus, especially type 2 diabetes, including the prevention of the sequelae associated therewith. Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Other disorders or conditions in which inflammatory reactions or cell differentiation may for example be involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   high blood pressure
   syndrome X
   polycystic ovary syndrome (PCOS)
   asthma
   osteoarthritis lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:
Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245, 744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:
Determination of EC50 Values of PPAR Agonists in the Cellular PPARalpha Assay
Principle The potency of substances which bind to human PPARalpha and activate in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARalpha ligands bind and activate the PPARalpha fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CG-GAGTACTGTCCTCCGAG-3') (SEQ ID No. 1) were cloned in 5'-upstream of a 68 bp-long minimal MMTV promoter (Genbank Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* gene (Genbank Accession # M15077) was cloned in 3'-downstream of the GAL4-MMTV element. After sequencing, the luceriferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3'-end of this GR-GAL4 construct. The fusion construct prepared in this way (GR-GAL4-humanPPARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500,000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 μM to 100 pM. More potent compounds are tested in concentration ranges from 1 μM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 μl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 31 in this assay are in the range from 0.1 nM to >10 μM.

The results for the activity of some compounds of the invention of the formula I are indicated in Table I below:

TABLE I

| Example No. | EC50 PPARalpha [nM] |
|---|---|
| II | 331 |
| VII | 469 |
| XI | 361 |

TABLE I-continued

| Example No. | EC50 PPARalpha [nM] |
|---|---|
| XIV | 106 |
| XV | 519 |
| XXI | 530 |
| XXIII | 222 |
| XXVI | 24 |

It is evident from Table I that the compounds of the invention of the formula I activate the PPARalpha receptor and thus bring about for example in analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345-52, 2001; S. Kersten et al.: Roles of PPARs in health and disease, NATURE, VOL 405, 25 May 2000, 421-4; I. Pineda et al.: Peroxisome proliferator-activated receptors: from transcriptional control to clinical practice, Curr Opin Lipidol 12: 2001, 245-254).

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5×GAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5×GAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3') (SEQ ID No. 2), together with a 160 bp-long thymidine kinase promoter section (Genbank Accession # AF027128) 5'-upstream into pGL3basic. 3'-downstream of the thymidine kinase promoter is the complete luciferase gene from *Photinus pyralis* (Genbank Accession # M15077) which is already a constituent of the plasmid pGL3basic used. The cloning and sequencing of the reporter plasmid pGL3basic-5×GAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession # P04386) into the plasmid pcDNA3 (from invitrogen) 3'-downstream of the cytomegalovirus promoter. Subsequently, the cDNA of the ligand-binding domain (LBD) of the human PPARgamma receptor (amino acids 1152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5×GAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (# 41965-039, Invitrogen), 100 µl of reference plasmid pRL-CMV (1 ng/µl), 100 µl of luciferase reporter plasmid pGL3basic-5×GAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µl). Then 2 ml of solution B are prepared by mixing 1.9 ml of DMEM (# 41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min. 80%-confluent HEK cells from a cell culture bottle with a capacity of 175 cm² are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (# 41965-039, Invitrogen) which is mixed with 10% FCS (# 16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µl of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (# 41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 µM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 6 nM to >10 µM were measured for the PPAR agonists described in this application.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The examples given below serve to illustrate the invention, but without limiting it.

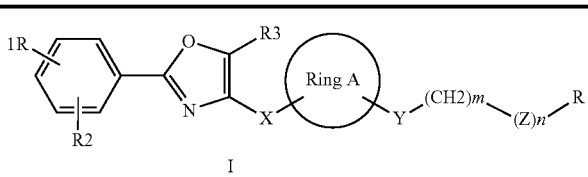

I

| | R1 | R2 | R3 | X | Y | ring A | m | n | Z | R |
|---|---|---|---|---|---|---|---|---|---|---|
| I | 3-Me | H | Me | CH2O | O | 1,3-Cy | 3 | 0 | — | 5-tetrazole |
| II | 3-Me | H | Me | CH2O | O | 1,3-Cy | 3 | 0 | — | NH—SO2CF3 |
| III | 3-Me | H | Me | CH2O | O | 1,3-Cy | 2 | 0 | — | 5-tetrazole |
| IV | 3-Me | H | Me | CH2O | O | 1,3-Cy | 2 | 0 | — | NH—SO2CF3 |
| V | 3-Me | H | Me | CH2O | O | 1,3-Cy | 2 | 0 | — | 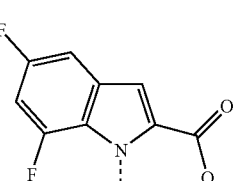 |
| VI | 3-Me | H | Me | CH2O | O | 1,3-Cy | 2 | 0 | — | 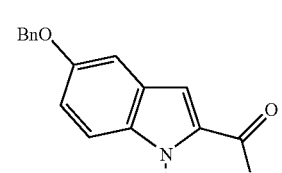 |
| VII | 3-Me | H | Me | CH2O | O | 1,3-Cy | 2 | 0 | — | 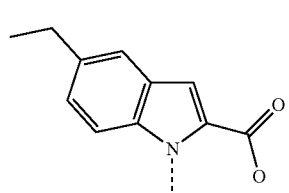 |

-continued
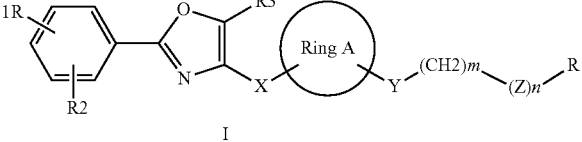
|  | R1 | R2 | R3 | X | Y | ring A | m | n | Z | R |
|---|---|---|---|---|---|---|---|---|---|---|
| VIII | 3-Me | H | Me | CH2O | O | 1,3-Cy | 2 | 0 | — | 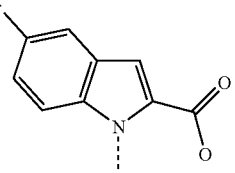 |
| IX | 3-Me | H | Me | CH2O | O | 1,3-Cy | 2 | 0 | — | 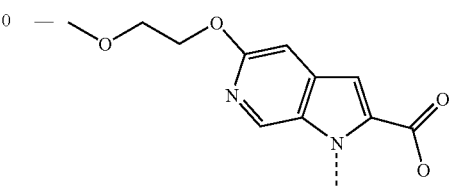 |
| X | 3-Me | H | Me | CH2O | O | 1,3-Cy | 2 | 0 | — | 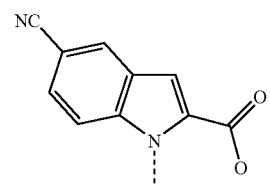 |
| XI | 3-Me | H | Me | CH2O | O | 1,3-Cy | 2 | 0 | — | 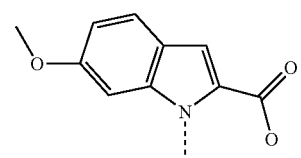 |
| XII | 3-Me | H | Me | CH2O | O | 1,3-Cy | 2 | 0 | — | 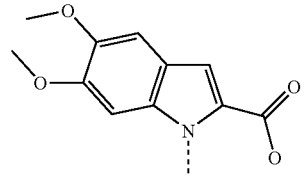 |
| XIII | 3-Me | H | Me | CH2O | O | 1,3-Cy | 2 | 0 | — | 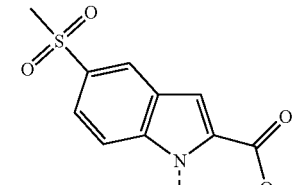 |
| XIV | 3-Me | H | Me | CH2O | O | 1,3-Cy | 2 | 1 | O | 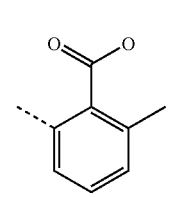 |

-continued

|     | R1   | R2 | R3 | X    | Y | ring A  | m | n | Z | R |
|-----|------|----|----|------|---|---------|---|---|---|---|
| XV    | 3-Me | H  | Me | CH2O | O | 1,3-Cy  | 2 | 1 | O | 2-carboxyphenyl |
| XVI   | 3-Me | H  | Me | CH2O | O | 1,3-Cy  | 2 | 1 | O | 2-carboxy-6-fluorophenyl |
| XVII  | 3-Me | H  | Me | CH2O | O | 1,3-Cy  | 2 | 1 | O | 2-carboxy-4-methoxyphenyl |
| XVIII | 3-Me | H  | Me | CH2O | O | 1,3-Cy  | 2 | 1 | O | 2-carboxy-6-methyl-4-isobutoxyphenyl |
| XIX   | 3-Me | H  | Me | CH2O | O | 1,3-Cy  | 2 | 1 | O | 2-carboxy-6-methyl-4-benzyloxyphenyl |
| XX    | 3-Me | H  | Me | CH2O | O | 1,3-Cy  | 2 | 1 | O | 2-nitrophenyl |

-continued

| | R1 | R2 | R3 | X | Y | ring A | m | n | Z | R |
|---|---|---|---|---|---|---|---|---|---|---|
| XXI | 3-Me | H | Me | CH2O | O | 1,3-Cy | 2 | 1 | O | 2-nitro-3-methylphenyl |
| XXII | 3-Me | H | Me | CH2O | O | 1,3-Cy | 2 | 1 | O | 2-(dihydroxyboryl)phenyl |
| XXIII | 3-Me | H | Me | CH2O | O | 1,3-Cy | 2 | 1 | O | 3-methyl-5-(trifluoromethyl)thiophene-2-carbonyl |
| XXIV | 3-Me | H | Me | CH2O | O | 1,3-Cy | 1 | 0 | — | 3-(trifluoromethylsulfonylamino)phenyl |
| XXV | 3-Me | H | Me | CH2O | O | 1,3-Cy | 1 | 0 | — | 2-(dihydroxyboryl)phenyl |
| XXVI | 4-Me | H | Me | CH2O | — | 1,3-Cy | 1 | 0 | — | indole-2-carbonyl (N-linked) |
| XXVII | 4-Me | H | Me | CH2O | — | 1,3-Cy | 1 | 0 | — | pyrrole-2-carbonyl (N-linked) |
| XXVIII | 3-OMe | H | Me | CH2O | — | 1,3-Cy | 1 | 0 | — | pyrrole-2-carbonyl (N-linked) |
| XXIX | 4-Me | H | Me | CH2O | — | 1,3-Cy | 1 | 1 | O | 3-methylthiophene-2-carbonyl |

-continued

| | R1 | R2 | R3 | X | Y | ring A | m | n | Z | R |
|---|---|---|---|---|---|---|---|---|---|---|
| XXX | 4-Me | H | Me | CH2O | — | 1,3-Cy | 1 | 1 | O | |
| XXXI | 4-Me | H | Me | CH2O | — | 1,3-Cy | 1 | 1 | O | |

Ring A: 1,3 Cy = cis-cyclohexane-1,3-diyl having the stereochemistry according to Cahn-Ingold-Prelog stated in the examples.
R: - - - denotes the point of attachment.

The compounds of the formula I can be obtained in accordance with the reaction schemes below:

Synthesis scheme I: Preparation of the central intermediates 6 and 7

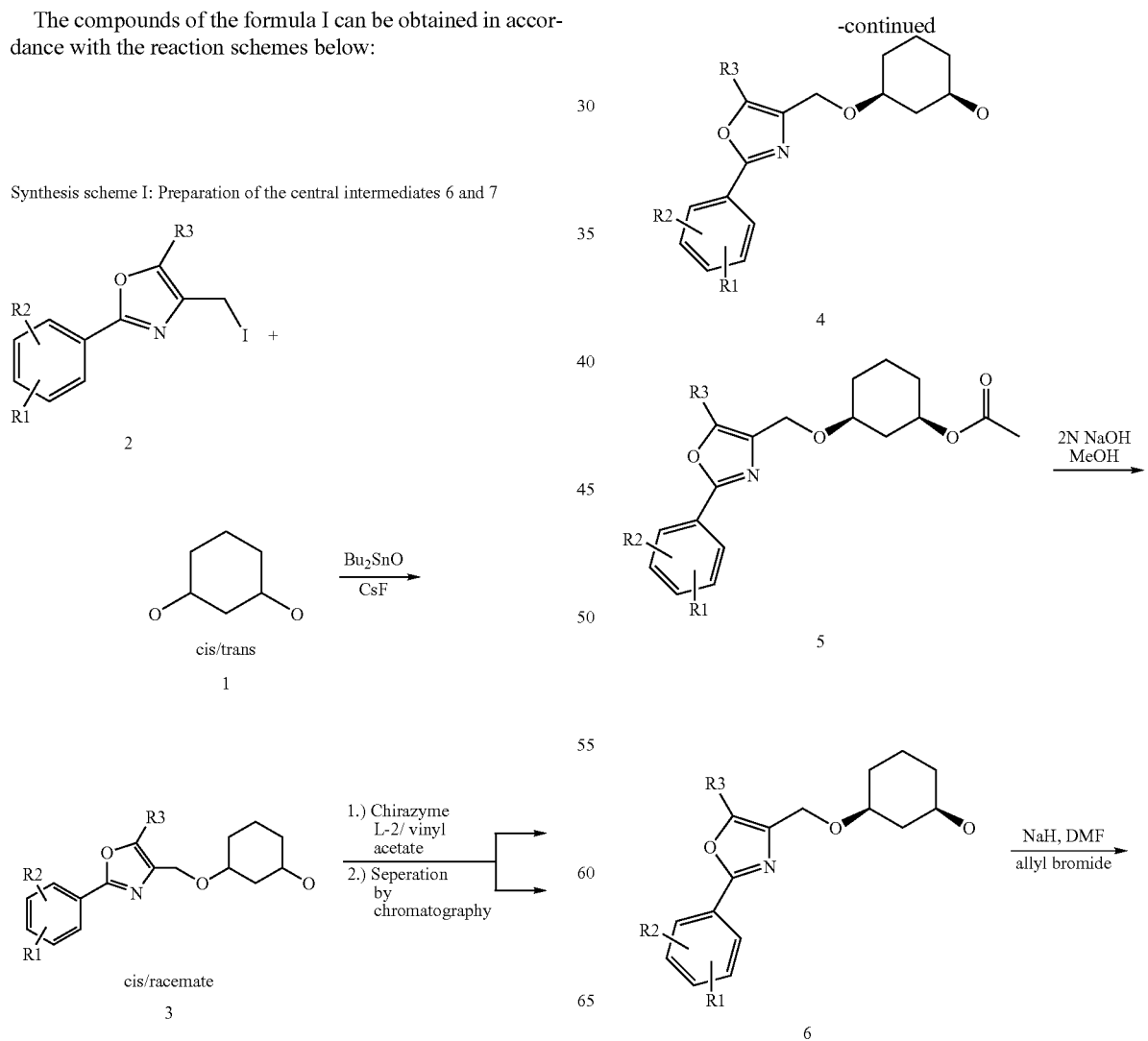

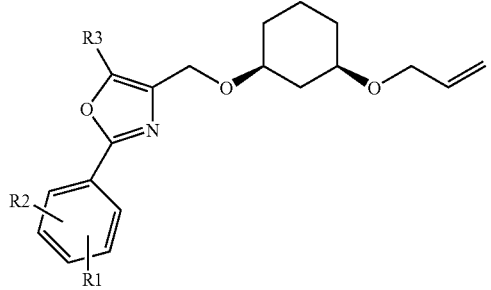
Synthesis scheme II: Functionalization of the allyl group in 7
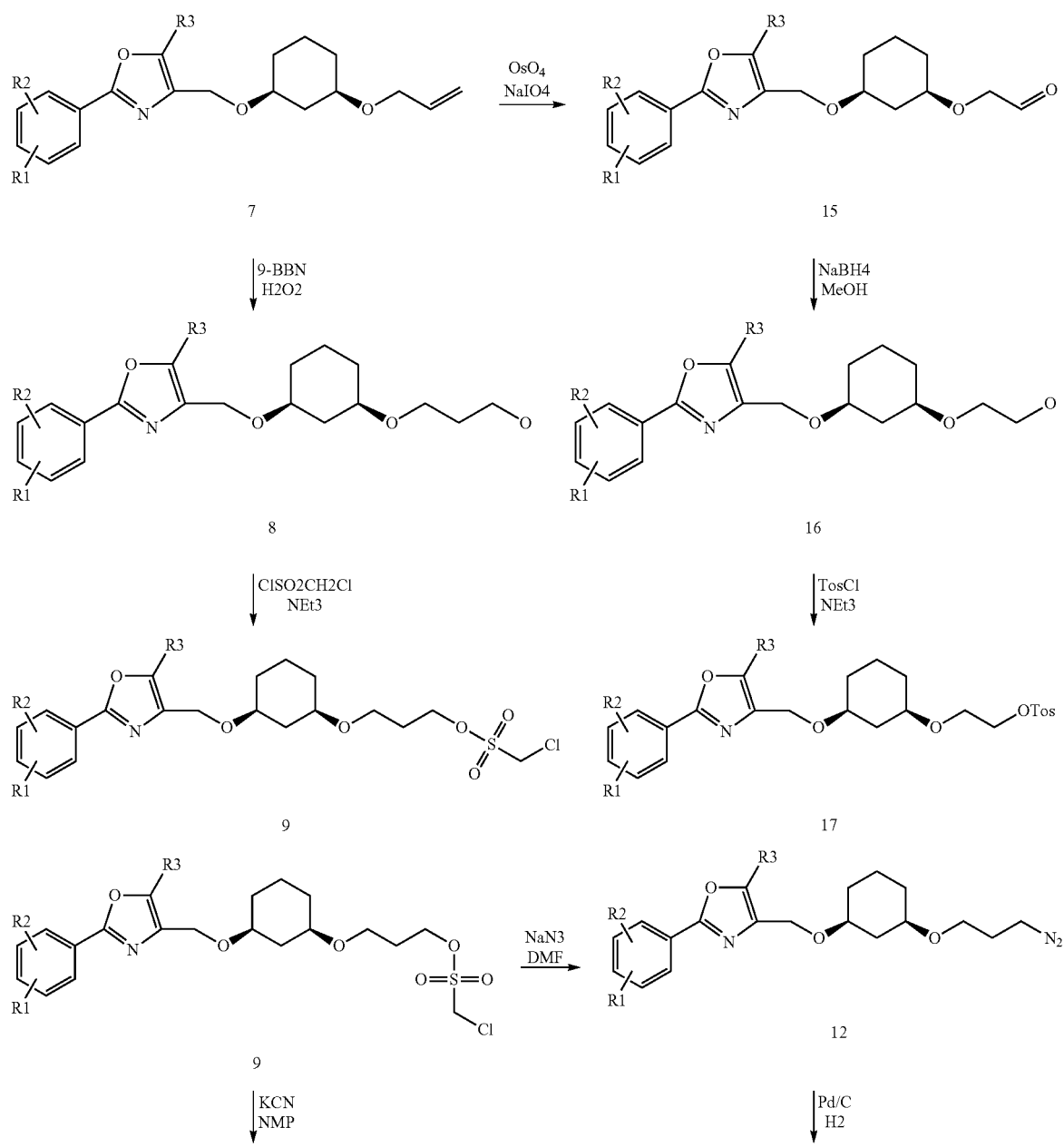

-continued
29
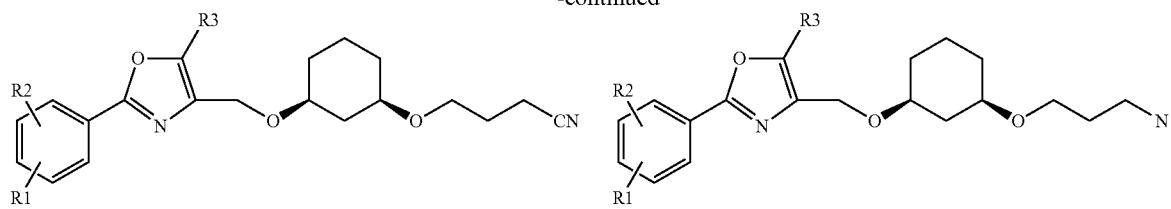
10
↓ BuSnN3
xylene
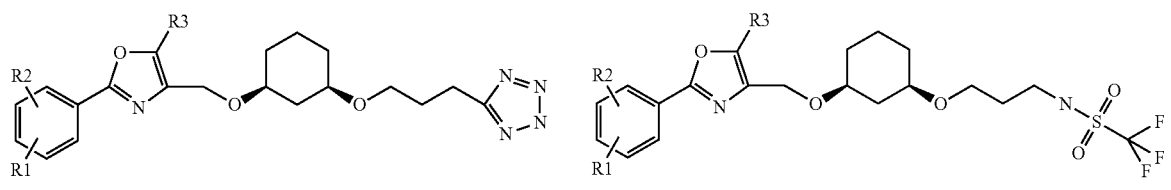
11
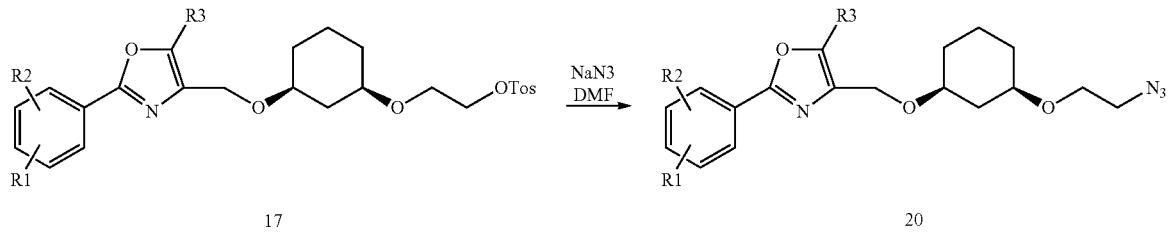
17
↓ KCN
NMP
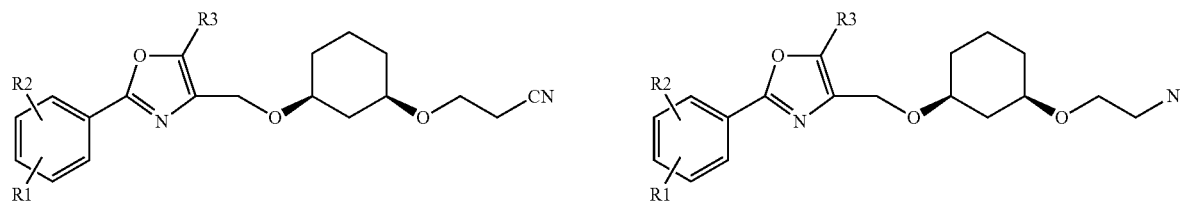
18
↓ MeSnN3
xylene
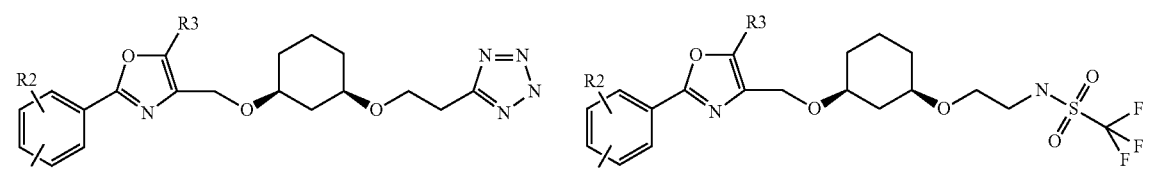
19
30
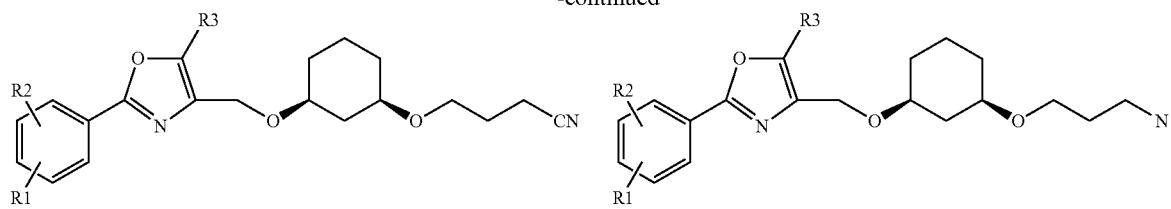
13
↓ Tt2O
NEt3
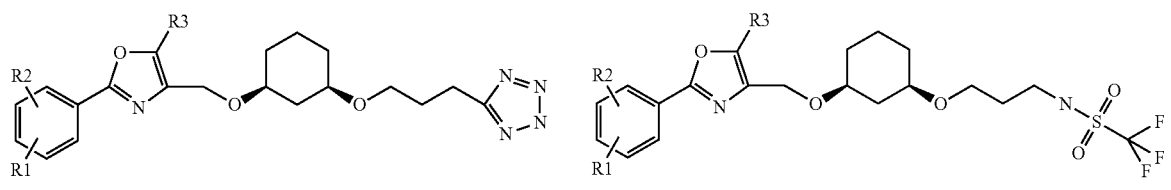
14
NaN3
DMF →
20
↓ Pd/C
H2
21
↓ Tt2O
NEt3
22

31 32
-continued
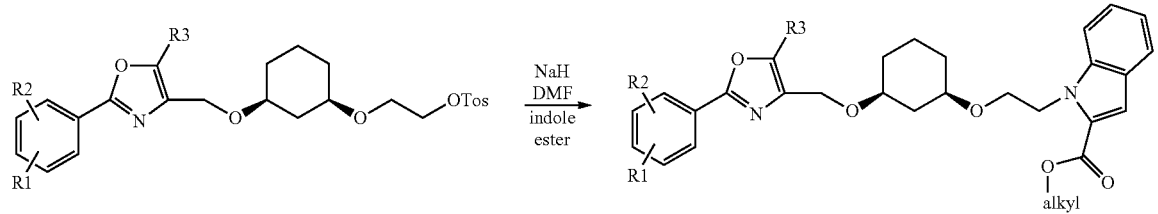
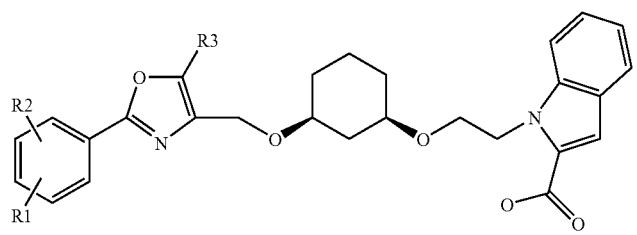
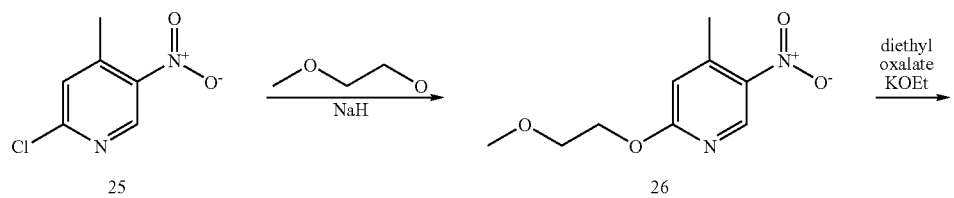
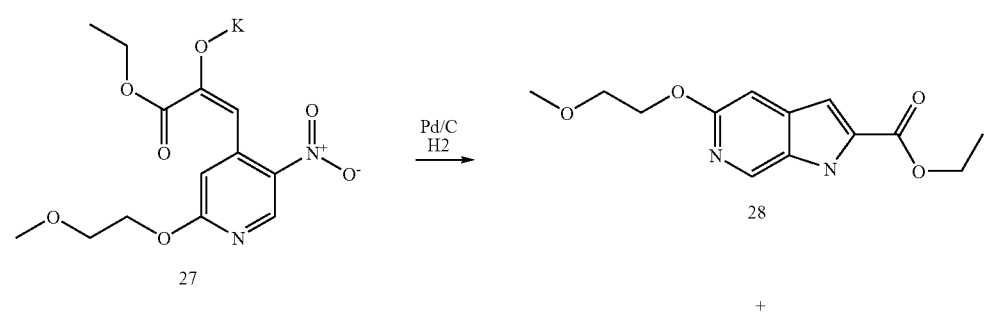
+
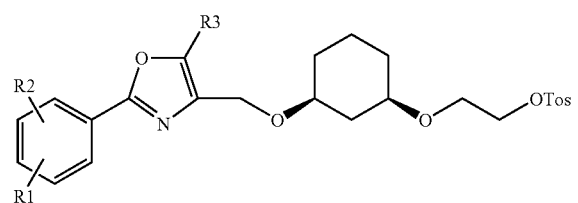

-continued
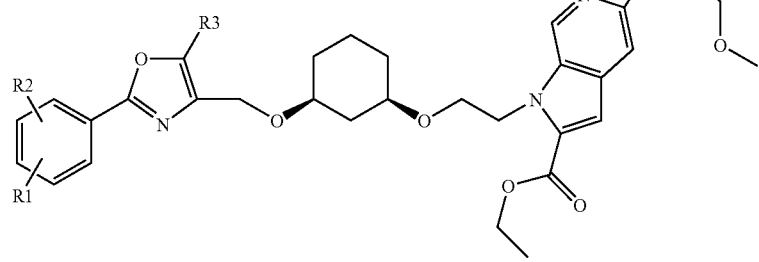
29
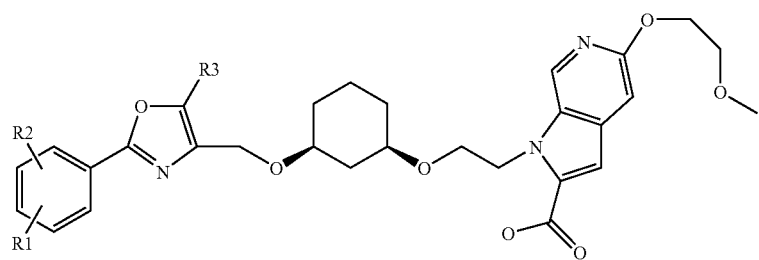
30
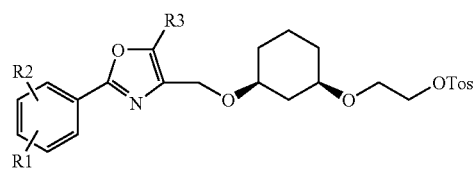 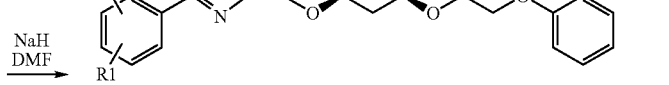
17 32
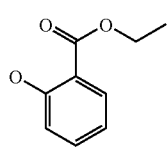
31
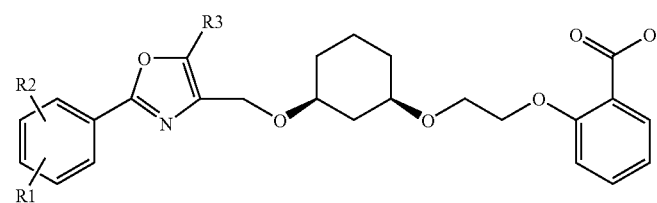
33

Synthesis scheme III: Reaction of 6 with functionalized benzyl bromides
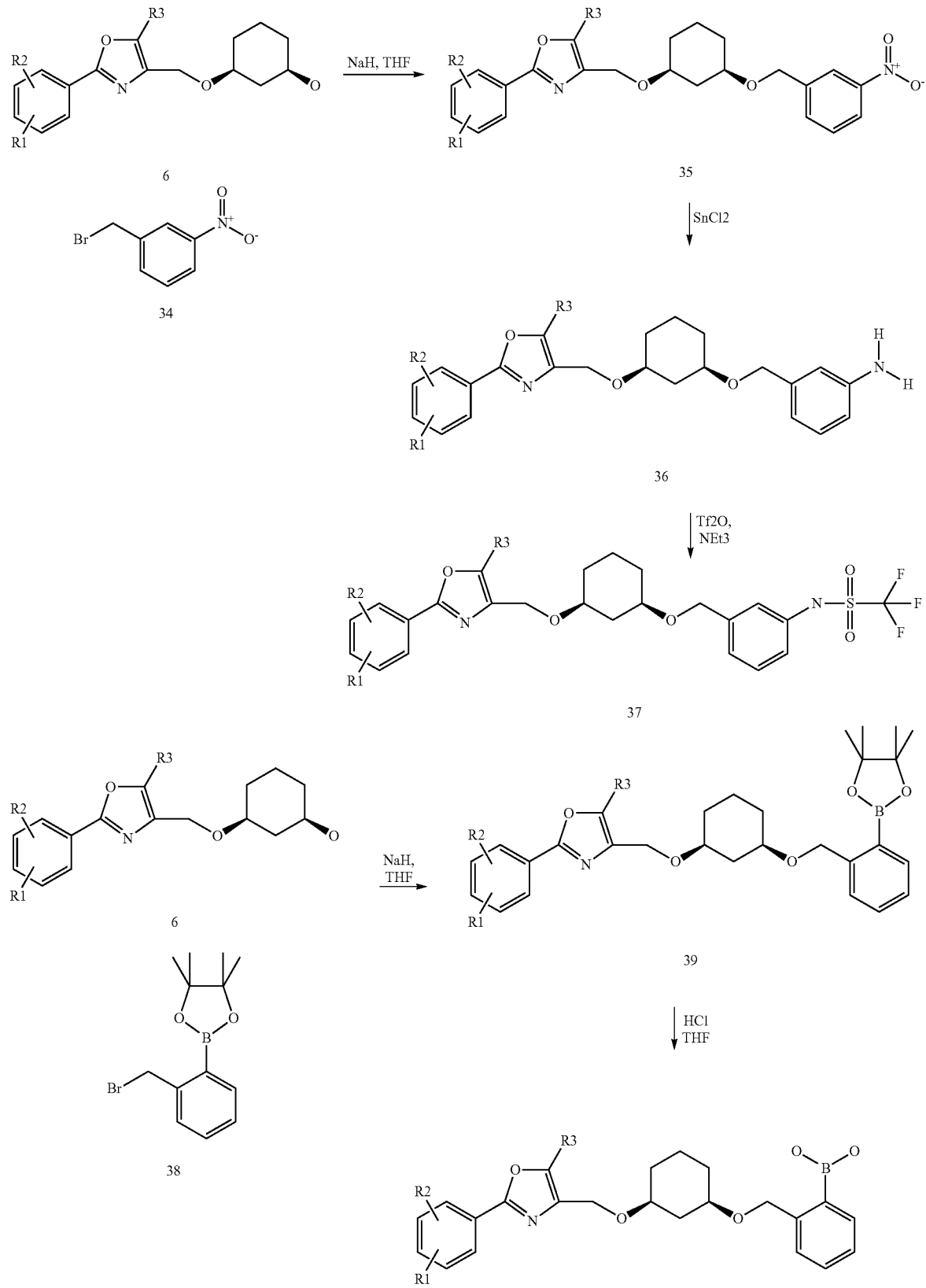

Synthesis scheme IV:
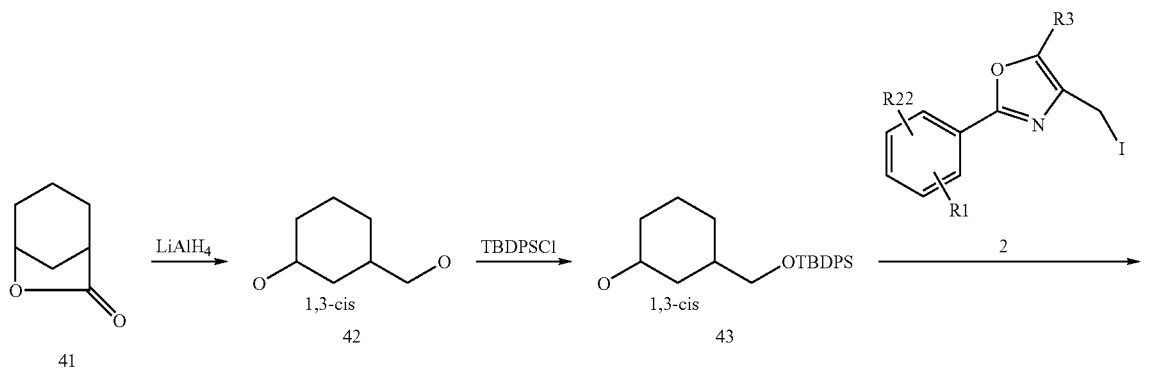
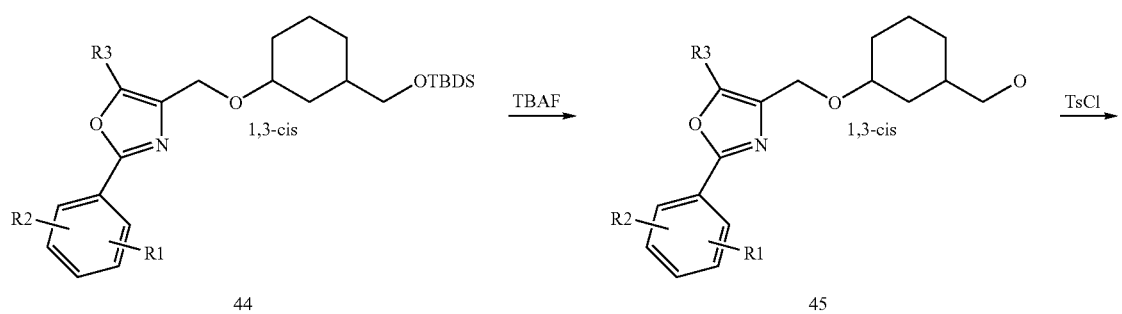
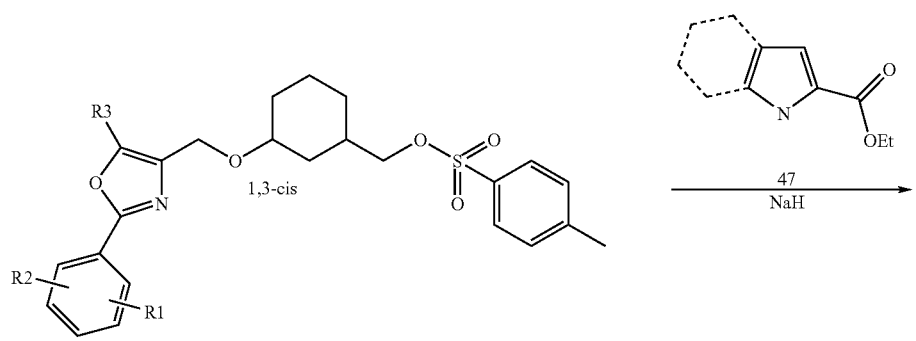
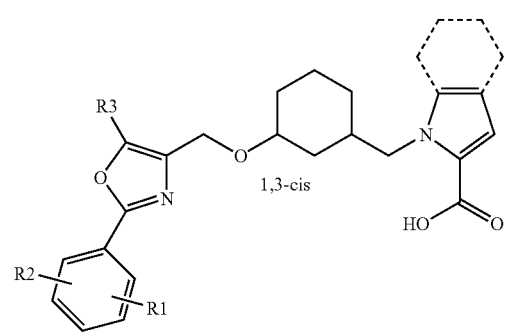

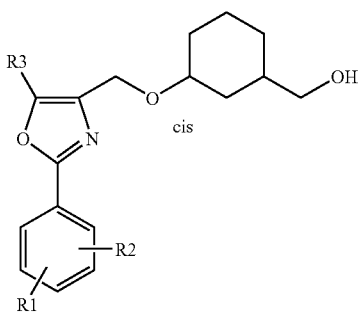

45

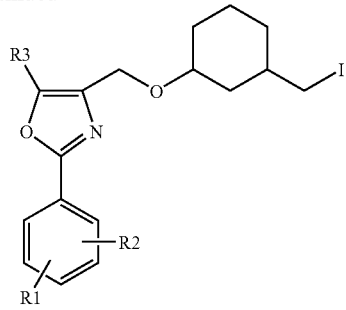

49

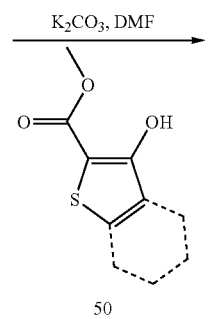

50

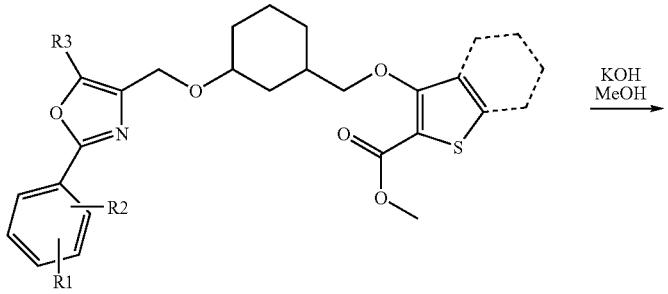

51

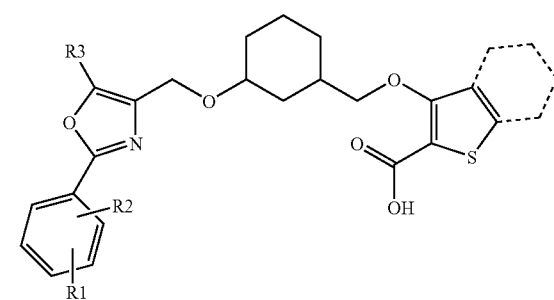

52

Here, component 1 is initially heated with dibutyltin oxide in toluene on a water separator for a plurality of hours and then, with addition of dimethylformamide, cesium fluoride and iodide 2, converted by stirring at room temperature for a number of hours into compounds of the general structure 3 in which R1, R2, R3 are as defined above.

The compound of the general formula 3 is reacted using Chirazyme L2 and vinyl acetate; this gives the compounds 4 and 5, of which 5, after separation, is reacted with alkali metal hydroxides to give compounds of the general structure 6 in which R1, R2, R3 are as defined above.

The compound of the general formula 6 is deprotonated using strong bases, for example sodium hydride in an aprotic solvent, and reacted with unsaturated bromides, for example allyl bromide, to give compounds of the general structure 7 in which R1, R2, R3 are as defined above.

The compound of the general formula 7 is, using hydroboration reagents, such as, for example, 9-BBN, and subsequent treatment with alkaline hydrogen peroxide, converted into compounds of the general structure 8, which is reacted with sulfonyl chlorides, for example chloromethylsulfonyl chloride, to give compounds of the general structure 9 in which R1, R2, R3 are as defined above.

Alternatively, the compound of the general formula 7 can be converted with osmium tetroxide and sodium periodate into the aldehyde of the general structure 15, which is reacted with complex hydrides, for example sodium borohydride, to give compounds of the general structure 16. The further conversion of compound of the general formula 16 with sulfonyl chlorides, for example toluenesulfonyl chloride, yields compounds of the general structure 17 in which R1, R2, R3 are as defined above.

Using sodium cyanide in aprotic solvents, such as, for example, NMP, the compound of the general formula 9 is converted into compounds of the general structure 10, which is reacted with a metal azide, for example tributyltin azide, to give compounds of the general structure 11 in which R1, R2, R3 are as defined above.

Alternatively, the compound of the general formula 9 can, using sodium azide in aprotic solvents, such as, for example, NMP, be converted into compounds of the general structure 12, which are, by catalytic hydrogenation using, for example, palladium-on-carbon, converted into the compounds of the general structure 13. The further reaction of compound of the general formula 13 with sulfonyl chlorides, for example trifluoromethanesulfonic anhydride, gives compounds of the general structure 14 in which R1, R2, R3 are as defined above.

The compound of the general formula 17 is, using sodium cyanide in aprotic solvents, such as, for example, NMP, converted into compounds of the general structure 18, which is reacted with a metal azide, for example tributyltin azide, to give compounds of the general structure 19 in which R1, R2, R3 are as defined above.

Alternatively, using sodium azide in aprotic solvents, such as, for example, NMP, the compound of the general formula 17 can be converted into compounds of the general structure 20, which are converted by catalytic hydrogenation, for example with palladium-on-carbon, into the compounds of the general structure 21. Further reaction of compound of the general formula 21 with sulfonyl chlorides, for example trifluoromethanesulfonic anhydride, gives compounds of the general structure 22 in which R1, R2, R3 are as defined above.

Nitrogen-containing aromatic heterocycles, for example pyrrole, indole, azaindole, are converted by treatment with strong bases, for example sodium hydride, in polar aprotic solvents, such as, for example, DMF, into the corresponding sodium salts and reacted with a compound of the general formula 17 to give compounds of the general structure 23 and 24. The compound of the general formula 24 is, using alkali metal hydroxides, converted into compounds of the general structure 23 in which R1, R2, R3 are as defined above.

Azaindole-2-carboxylic esters of type 28 are prepared by nucleophilic aromatic substitution on 2-chloronitropyridines (25) with alkoxides and subsequent condensation with oxalic esters. Reductive cyclization under an atmosphere of hydrogen gives azaindole-2-carboxylic esters of type 28 which can be reacted as described above with a compound of the general formula 17 to give compounds of the general structure 29. Following hydrolysis of the ester compounds of the general structure 30 similar to compounds of the general structure 22.

Benzoic esters substituted by a hydroxyl group of the general formula 31 and heterocyclic carboxylic esters, for example thiophene and furan, are converted by treatment with strong bases, for example sodium hydride, in polar aprotic solvents, such as, for example, DMF, into the corresponding sodium salts and reacted with a compound of the general formula 17 to give compounds of the general structure 32. The compound of the general formula 32 is, using alkali metal hydroxides, converted into compounds of the general structure 33 in which R1, R2, R3 are as defined above.

The compound of the general formula 6 is deprotonated in an aprotic solvent using strong bases, for example sodium hydride, and reacted with benzyl bromides of the general formula 34 to give compounds of the general structure 35. The compound of the general formula 35 is, using a reducing agent, for example tin(II) chloride, in an aprotic solvent, converted into compounds of the general formula 36, which with trifluoromethanesulfonic anhydride into the sulfonamides of the general formula 37 in which R1, R2, R3 are as defined above.

The compound of the general formula 6 is deprotonated using strong bases, for example sodium hydride in an aprotic solvent, and reacted with benzyl bromides of the general formula 38 to give compounds of the general structure 39. The compound of the general formula 39 is reacted with aqueous acid to give compounds of the general formula 40 in which R1, R2, R3 are as defined above.

Using lithium aluminum hydride, the lactone 41 is reduced to diol 42 which can be protected by selective monosilylation (43). The compound of the general formula 43 is deprotonated using strong bases, for example sodium hydride in an aprotic solvent, and reacted with phenyloxazoyl iodides of the general formula 2 to give compounds of the general structure 44. The compound of the general formula 45 is desilylated with fluoride, for example TBAF, giving compounds of the general formula 45, which are reacted with sulfonyl chloride, for example toluenesulfonyl chloride, to give compounds of the general formula 46 in which R1, R2, R3 are as defined above.

Nitrogen-containing aromatic heterocycles of the general formula 47, for example pyrrole, indole, azaindole, are converted by treatment with strong bases, for example sodium hydride, in polar aprotic solvents, such as, for example, DMF, into the corresponding sodium salts and reacted with a compound of the general formula 48 in which R1, R2, R3 are as defined above.

Heterocyclic carboxylic esters substituted by a hydroxyl group, for example thiophene and benzothiophene are in the deprotonated in the presence of weak bases, for example potassium carbonate, in polar aprotic solvents, such as, for example, DMF, and reacted with a compound of the general formula 49 to give compounds of the general structure 51. The compound of the general formula 51 is converted using alkali metal hydroxides into compounds of the general structure 52 in which R1, R2, R3 are as defined above.

Other compounds of the formula I can be prepared accordingly or by known processes.

EXAMPLES

The examples and preparation methods given below serve to illustrate the invention, but without limiting it.

rac-3-(cis-5-Methyl-2-m-tolyloxazol-4-ylmethoxy) cyclohexanol

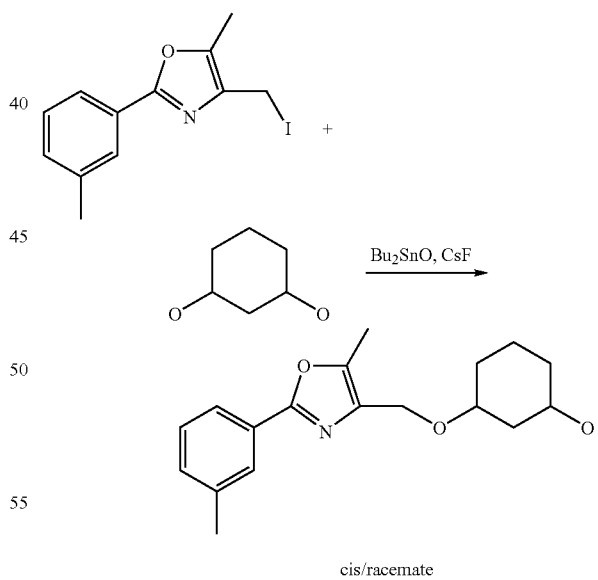

cis/racemate 21.7 g of 1,3-cyclohexanediol and 30.3 g of dibutyltin oxide are dissolved in 450 ml of toluene and, under reflux on a water separator, heated at the boil. During the reaction time, the reaction volume is reduced by half. After three hours, the reaction mixture is cooled to room temperature and 300 ml of DMF, 29 g of 4-iodomethyl-5-methyl-2-m-tolyloxazole and 23.5 g of cesium fluoride are added. The mixture is stirred at room temperature for 18 hours. The reaction mixture is diluted by addition of ethyl acetate and washed with saturated NaCl solution. The organic phase is dried over magnesium sulfate, the solvent is removed under reduced pressure and the residue is purified by flash chromatography on silica gel (n-heptane/ethyl acetate=10:1->1:4). This gives 58 g of the cis-3-(5-methyl-2-m-tolyloxazol-4-ylmethoxy)cyclohexanol racemate as a yellowish solid which is recrystallized from n-heptane/ethyl acetate. $C_{18}H_{23}NO_3$ (301.39), MS (ESI): 302 (M+H$^+$).

3-((1R,3S)-cis-5-Methyl-2-m-tolyloxazol-4-ylmethoxy)cyclohexanol

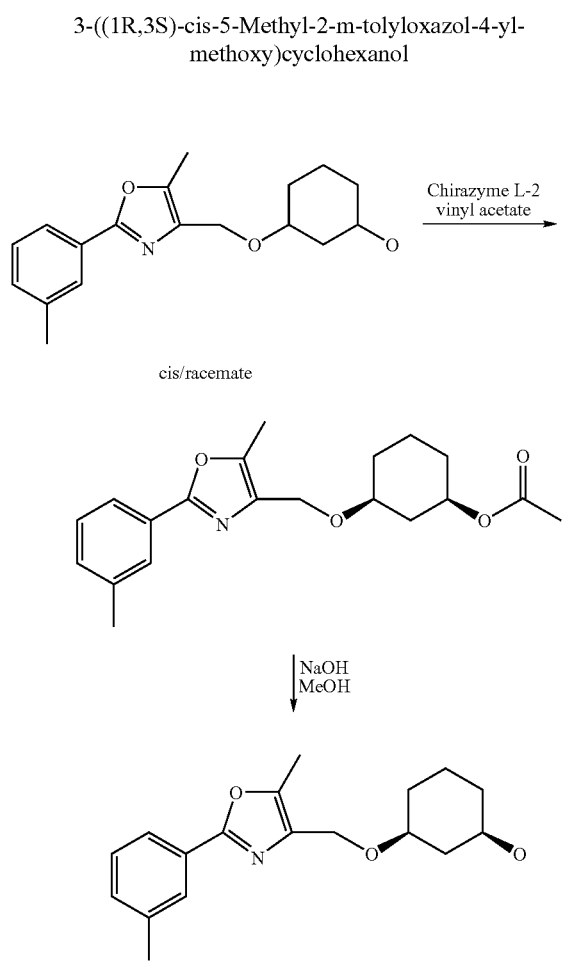

25 g of racemic cis-3-(5-methyl-2-m-tolyloxazol-4-ylmethoxy)cyclohexanol are dissolved in 320 ml of vinyl acetate and 1.3 g of chirazyme L-2 Lyo (Boehringer Mannheim) are added. After about three hours of stirring at room temperature (LC-MS control for a conversion of 40-45%) the enzyme is filtered off and washed with ethyl acetate and the solvent is removed under reduced pressure. The residue is purified by flash chromatography on silica gel (n-heptane/ethyl acetate=3:1). This gives 8 g of the (1R,3S)-3-(5-methyl-2-m-tolyloxazol-4-ylmethoxy)-cyclohexyl acetate as colorless oil. $C_{20}H_{25}NO_4$ (343.43), MS (ESI): 344 (M+H$^+$), the acetate is taken up in 170 ml of methanol and, after addition of 27 ml of 2N NaOH, stirred at room temperature for one hour. Most of the solvent is removed under reduced pressure. After addition of in each case 150 ml of water and ethyl acetate, the org. phase is washed with NaCl solution. The organic phase is dried over magnesium sulfate, the solvent is removed under reduced pressure. This gives 6.7 g of 3-((1R, 3S)-5-methyl-2-m-tolyloxazol-4-ylmethoxy)cyclohexanol as a yellowish solid. $C_{18}H_{23}NO_3$ (301.39), MS (ESI): 302 (M+H$^+$).

4-((1R,3S)-3-Allyloxycyclohexyloxymethyl)-5-methyl-2-m-tolyloxazole

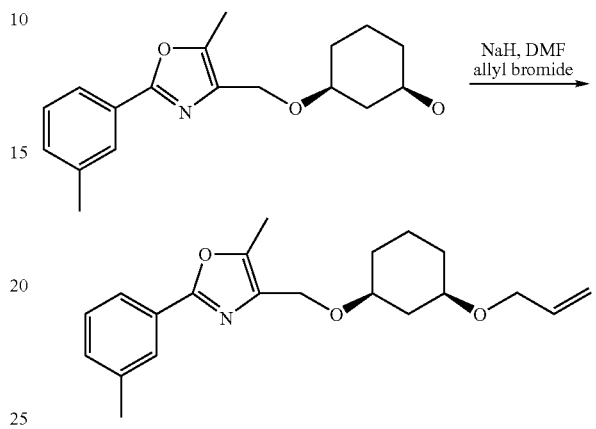

At room temperature, 470 mg of a 60 percent strength suspension of sodium hydride are added to a solution of 2.2 g of 3-((1R,3S)-5-methyl-2-m-tolyloxazol-4-ylmethoxy)cyclohexanol in 30 ml of dimethylformamide, and the mixture is stirred at room temperature for 20 min. 1.36 ml of allyl bromide are then added, the mixture is stirred at 40° C. until the conversion is complete, and, if necessary, further sodium hydride and ally bromide are added. Once the conversion is complete (monitored by LC-MS), 100 ml of ethyl acetate and 150 ml of sat. NaCl solution are added. The organic phase is dried over magnesium sulfate, the solvents are removed under reduced pressure and the residue is purified by flash chromatography on silica gel (n-heptane/ethyl acetate=3:1). This gives 2.3 g of 4-((1R,3S)-3-allyloxycyclohexyloxymethyl)-5-methyl-2-m-tolyloxazol 5 as a colorless oil. $C_{21}H_{27}NO_3$ (341.45), MS (ESI): 342 (M+H$^+$).

3-(1R,3S)-[3-(5-Methyl-2-m-tolyloxazol-4-ylmethoxy)cyclohexyloxy]propan-1-ol

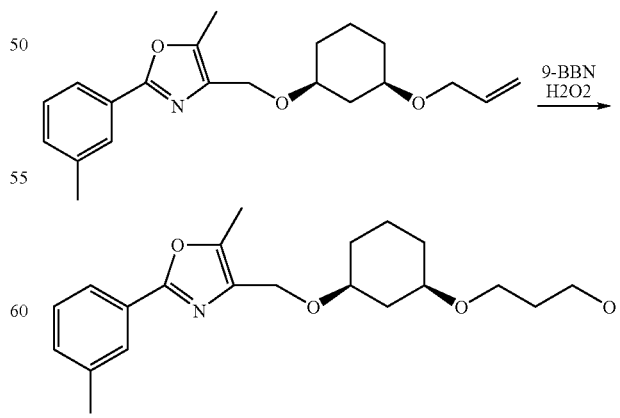

3.3 g of 4-((1R,3S)-3-(Allyloxycyclohexyloxymethyl)-5-methyl-2-m-tolyloxazole are dissolved in 70 ml of dry THF and, at room temperature, 20 ml of 9-BBN, 0.5 M in THF, are added. The mixture is stirred at this temperature for 4 h and 10 ml of water, 10 ml of 2 N NaOH and 5 ml of 30% strength H₂O₂ are added successively. The mixture is stirred at room temperature for 18 h and then heated at 40° C. for 1 h. After cooling, 50 ml of water are added, the mixture is extracted twice with 100 ml of methyl tert-butyl ether and the combined org. phases are washed with sat. NaCl solution. The organic phases are dried over sodium sulfate and the solvent is removed under reduced pressure. The residue is purified by flash chromatography on silica gel (n-heptane/ethyl acetate=1:2). This gives 1.56 g of 3-(1R,3S)-[3-(5-methyl-2-m-tolyloxazol-4-ylmethoxy)cyclohexyloxy]propan-1-ol as a colorless oil. $C_{21}H_{29}NO_4$ (359.47), MS (ESI): 360 (M+H$^+$).

((1R,3S)-3-[3-(5-methyl-2-m-tolyloxazol-4-ylmethoxy)cyclohexyloxy]propyl 4-chloromethanesulfonate

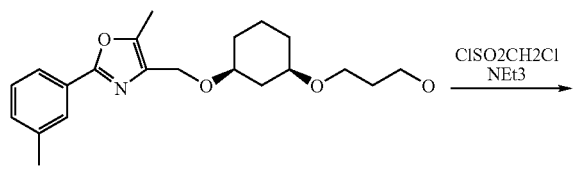

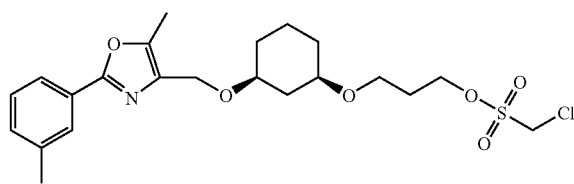

1.56 g of 3-(1R,3S)-[3-(5-methyl-2-m-tolyloxazol-4-ylmethoxy)cyclohexyloxy]propan-1-ol are dissolved in 15 ml of dichloromethane, and, at 0° C., 0.7 ml of pyridine and 0.45 ml of chloromethanesulfonyl chloride are added. After five hours of stirring at this temperature, the mixture is poured onto ice/1 N HCl and extracted with dichloromethane. The extract is dried over sodium sulfate and the solvent is removed under reduced pressure. The residue is purified by flash chromatography on silica gel (n-heptane/ethyl acetate=1:1). This gives 1.8 g of ((1R,3S)-3-[3-(5-methyl-2-m-tolyloxazol-4-ylmethoxy)cyclohexyloxy]propyl 4-chloromethanesulfonate as a colorless oil. $C_{22}H_{30}ClNO_4S$ (472.00), MS (ESI): 473 (M+H$^+$), 2-((1R,3S)-[3-(5-Methyl-2-m-tolyloxazol-4-ylmethoxy)cyclohexyloxy]ethanol

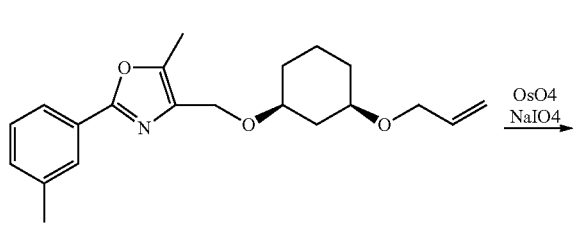

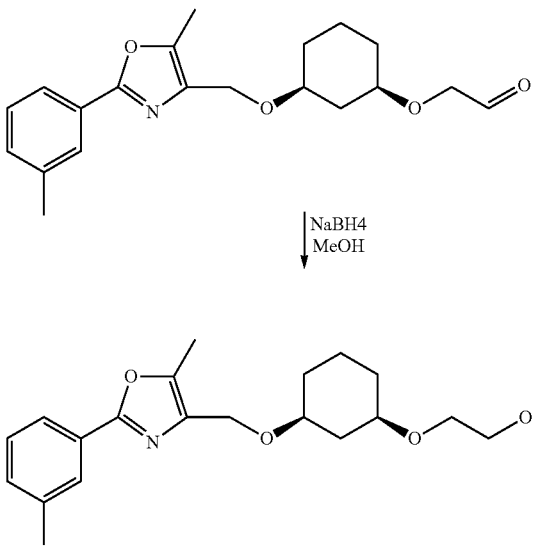

2.3 g of 4-((1R,3S)-3-(allyloxycyclohexyloxymethyl)-5-methyl-2-m-tolyloxazole are dissolved in 65 ml of methyl tert-butyl ether and, at 0° C., 65 ml of water, 4.4 g of sodium metaperiodate and 3.3 ml of a 2.5% strength solution of osmium tetroxide in tert-butanol are added. After 20 min, the mixture is slowly warmed to 40° C. After 2 h, a further 700 mg of sodium metaperiodate were added and the mixture was stirred at 45° C. for 2 h. 140 ml of sat. sodium thiosulfate solution were added and the mixture was extracted with methyl tert-butyl ether. The combined organic phases are dried over sodium sulfate and the solvent is removed under reduced pressure. This gives 2-((1R,3S)-[3-(5-methyl-2-m-tolyloxazol-4-ylmethoxy)cyclohexyloxy]acetaldehyde as a colorless oil. $C_{20}H_{25}NO_4$ (343.43), MS (ESI): 344 (M+H$^+$). 2-((1R,3S)-[3-(5-Methyl-2-m-tolyloxazol-4-ylmethoxy)cyclohexyloxy]acetaldehyde is, as a crude product, taken up in 60 ml of dry methanol, and 300 mg of sodium borohydride are added. After 1.5 h, the mixture is quenched with 3 ml of acetone and concentrated. The residue is taken up in 50 ml of ethyl acetate/50 ml of sat. sodium bicarbonate solution, and the org. phase is dried over sodium sulfate. The solvent is removed under reduced pressure and the residue is then purified by flash chromatography on silica gel (n-heptane/ethyl acetate=1:3). This gives 1.6 g of 2-((1R,3S)-[3-(5-methyl-2-m-tolyloxazol-4-ylmethoxy)cyclohexyloxy]ethanol as a colorless oil. $C_{20}H_{27}NO_4$ (345.44), MS (ESI): 346 (M+H$^+$).

((1R,3S)-[3-(5-Methyl-2-m-tolyloxazol-4-yl-methoxy)cyclohexyloxy]ethyl toluene-4-sulfonate

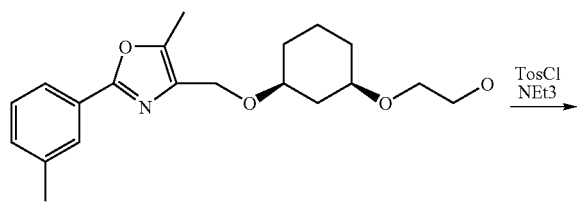

1.6 g of 2-((1R,3S)-[3-(5-methyl-2-m-tolyloxazol-4-yl-methoxy)cyclohexyloxy]ethanol are dissolved in a mixture of 30 ml of dichloromethane and 3.6 ml of pyridine, and 1.2 g of 4-tosyl chloride and 50 mg of dimethylaminopyridine are added. The mixture is stirred at room temperature for 18 h and then poured into 2 N HCl/ice, and the aqueous phase is extracted with 50 ml of dichloromethane. The combined organic phases are dried over sodium sulfate and the solvent is removed under reduced pressure. The residue is purified by flash chromatography on silica gel (n-heptane/ethyl acetate=2:1). This gives ((1R,3S)-[3-(5-methyl-2-m-tolyloxazol-4-ylmethoxy)cyclohexyloxy]ethyl toluene-4-sulfonate as a colorless oil. $C_{27}H_{33}NO_6S$ (513.66), MS (ESI): 514 (M+H$^+$).

Example I (1R,3S)-5-{3-[3-(5-Methyl-2-m-tolyloxazol-4-yl-methoxy)cyclohexyloxy]-propyl}-2H-tetrazole (1R,3S)-4-[3-(5-Methyl-2-m-tolyloxazol-4-yl-methoxy)cyclohexyloxy]butyronitrile

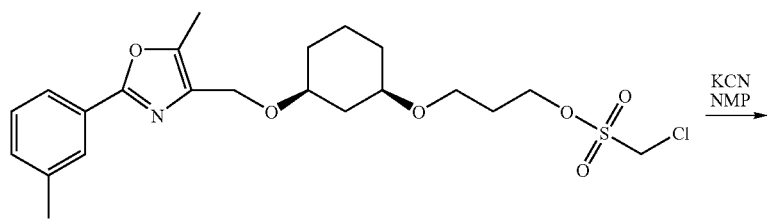

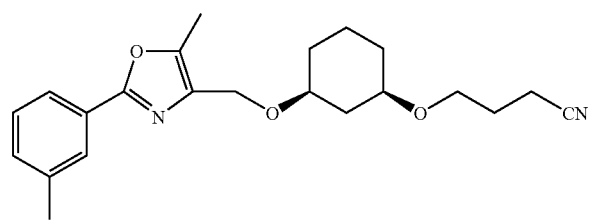

472 mg of ((1R,3S)-3-[3-(5-methyl-2-m-tolyloxazol-4-yl-methoxy)cyclohexyloxy]propyl 4-chloromethanesulfonate are dissolved in 3 ml of N-methylpyrrolidone, and 200 mg of potassium cyanide and 30 mg of tetrabutylammonium iodide are added. The mixture is stirred at 60° C. for 3 h and, after cooling, taken up in 20 ml of ethyl acetate/20 ml with sat. NaCl solution. The organic phase is dried over sodium sulfate and the solvent is removed under reduced pressure. The residue is purified by flash chromatography on silica gel (n-heptane/ethyl acetate=1:1). This gives (1R,3S)-4-[3-(5-methyl-2-m-tolyloxazol-4-ylmethoxy)cyclohexyloxy]butyronitrile as a colorless oil. $C_{22}H_{28}N_2O_3$ (368.48), MS (ESI): 369 (M+H$^+$).

(1R,3S)-5-{3-[3-(5-Methyl-2-m-tolyloxazol-4-yl-methoxy)cyclohexyloxy]propyl}-2H-tetrazole

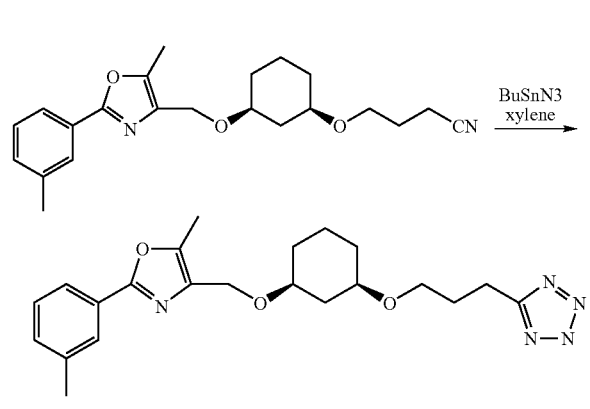

333 mg of (1R,3S)-4-[3-(5-methyl-2-m-tolyloxazol-4-yl-methoxy)cyclohexyloxy]butyronitrile are dissolved in 5 ml of xylene, and 919 mg of tributyltin azide are added. The mixture is stirred at 120° C. for 18 h and, after cooling, titurated with 0.5 ml of TFA. The solvent is removed under reduced pressure and the residue is purified by RP-HPLC. This gives (1R,3S)-5-{3-[3-(5-methyl-2-m-tolyloxazol-4-yl-methoxy)cyclohexyloxy]propyl}-2H-tetrazole as a colorless oil. $C_{22}H_{29}N_5O_3$ (411.51), MS (ESI): 412 (M+H$^+$).

Example II (1R,3S)—C,C,C-Trifluoro-N-{3-[3-(5-methyl-2-m-tolyloxazol-4-ylmethoxy)cyclohexyloxy]propyl}methanesulfonamide (1R,3S)-3-[3-(5-Methyl-2-m-tolyloxazol-4-ylmethoxy)cyclohexyloxy]propylamine

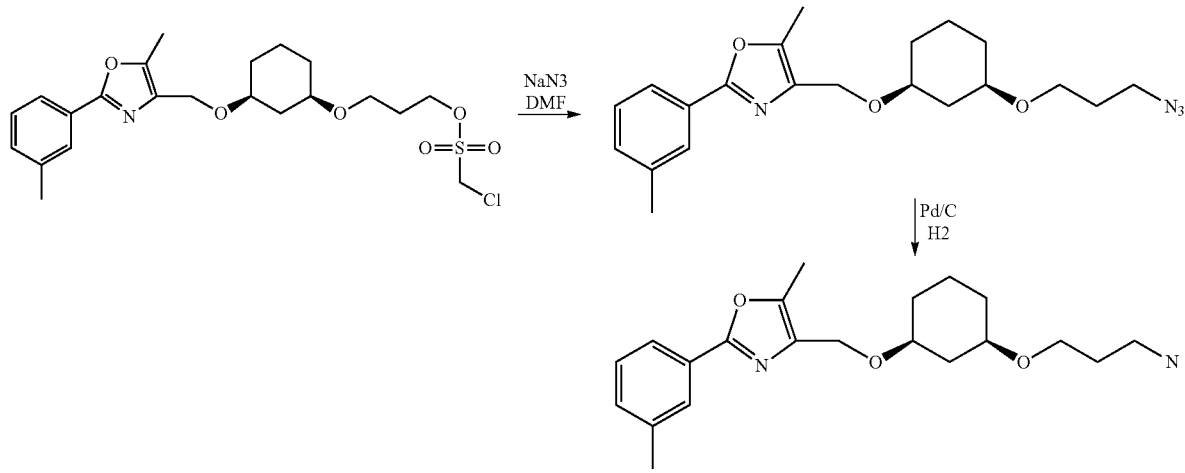

472 mg of ((1R,3S)-3-[3-(5-methyl-2-m-tolyloxazol-4-ylmethoxy)cyclohexyloxy]propyl 4-chloromethanesulfonate are dissolved in 3 ml of N-methylpyrrolidone, and 200 mg of sodium azide are added. The mixture is stirred at 60° C. for 3 h and, after cooling, taken up in 20 ml of ethyl acetate/20 ml with sat. NaCl solution. The organic phase is dried over sodium sulfate and the solvent is removed under reduced pressure. This gives 4-((1R,3S)-[3-(3-azidopropoxy)cyclohexyloxymethyl]-5-methyl-2-m-tolyloxazole as a colorless oil. $C_{21}H_{28}N_4O_3$ (384.48), MS (ESI): 385 (M+H$^+$). The crude azide is taken up in 20 ml of methanol and hydrogenated with 50 mg of Pd/C 10% at a hydrogen atmosphere of 1 bar for 3 h. The catalyst is filtered off, giving (1R,3S)-3-[3-(5-methyl-2-m-tolyloxazol-4-ylmethoxy)cyclohexyloxy]propylamine as a colorless oil. $C_{21}H_{30}N_2O_3$ (358.48), MS (ESI): 359 (M+H$^+$).

(1R,3S)—C,C,C-Trifluoro-N-{3-[3-(5-methyl-2-m-tolyloxazol-4-ylmethoxy)cyclohexyloxy]propyl}methanesulfonamide

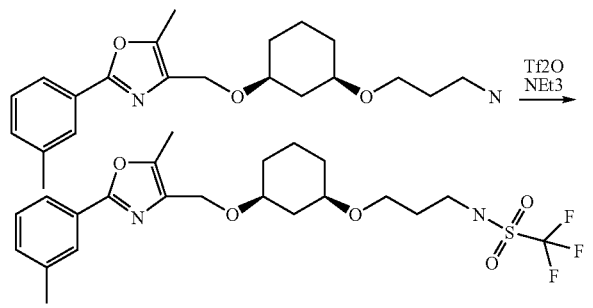

95 mg of (1R,3S)-3-[3-(5-methyl-2-m-tolyloxazol-4-ylmethoxy)cyclohexyloxy]propylamine are dissolved in 2 ml of dichloromethane, 0.1 ml of triethylamine are added and the mixture is cooled to −78° C. 60 μl of trifluoromethanesulfonic anhydride are added, and the mixture is slowly allowed to warm to room temperature. After 3 h all volatile components were removed under reduced pressure and the residue was taken up in DMF and filtered. The compound is purified by RP-HPLC. This gives (1R,3S)—C,C,C-trifluoro-N-{3-[3-(5-methyl-2-m-tolyloxazol-4-ylmethoxy)cyclohexyloxy]propyl}methanesulfonamide as a colorless oil. $C_{22}H_{29}F_3N_2O_5S$ (490.55), MS (ESI): 491 (M+H$^+$).

Example III (1R,3S)-5-{3-[3-(5-Methyl-2-m-tolyloxazol-4-ylmethoxy)cyclohexyloxy]ethyl}-2H-tetrazole (1R,3S)-4-[3-(5-Methyl-2-m-tolyloxazol-4-ylmethoxy)cyclohexyloxy]propionitrile

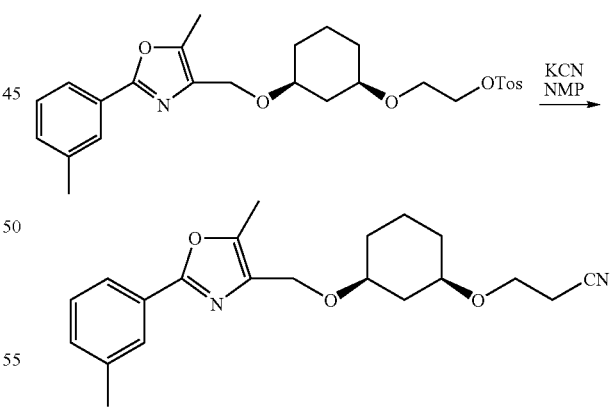

500 mg of ((1R,3S)-[3-(5-methyl-2-m-tolyloxazol-4-ylmethoxy)cyclohexyloxy]ethyl toluene-4-sulfonate are dissolved in 3 ml of N-methylpyrrolidone, and 200 mg of potassium cyanide and 30 mg of tetrabutylammonium iodide are added. The mixture is stirred at 50° C. for 8 h and, after cooling, taken up in 20 ml of ethyl acetate/20 ml with sat. NaCl solution. The organic phase is dried over sodium sulfate and the solvent is removed under reduced pressure. This gives (1R,3S)-4-[3-(5-methyl-2-m-tolyloxazol-4-ylmethoxy)cyclohexyloxy]propionitrile as a colorless oil. $C_{22}H_{28}N_2O_3$ (368.48), MS (ESI): 369 (M+H⁺).

(1R,3S)-5-{3-[3-(5-Methyl-2-m-tolyloxazol-4-yl-methoxy)cyclohexyloxy]ethyl}-2H-tetrazole

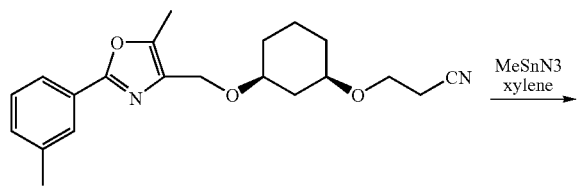

100 mg of (1R,3S)-4-[3-(5-methyl-2-m-tolyloxazol-4-yl-methoxy)cyclohexyloxy]propionitrile are dissolved in 5 ml of xylene, and 82 mg of trimethyltin azide are added. The mixture is stirred at 130° C. for 24 h and, after cooling, titurated with 0.5 ml of TFA. The solvent is removed under reduced pressure and the residue is purified by RP-HPLC. This gives (1R,3S)-5-{3-[3-(5-methyl-2-m-tolyloxazol-4-yl-methoxy)cyclohexyloxy]ethyl}-2H-tetrazole as a colorless oil. $C_{21}H_{27}N_5O_3$ (397.48), MS (ESI): 398 (M+H⁺).

Example IV (1R,3S)—C,C,C-Trifluoro-N-{3-[3-(5-methyl-2-m-tolyloxazol-4-ylmethoxy)cyclohexyloxy]ethyl}-methanesulfonamide (1R,3S)-3-[3-(5-Methyl-2-m-tolyloxazol-4-yl-methoxy)cyclohexyloxy]ethylamine 500 mg of ((1R,3S)-[3-(5-methyl-2-m-tolyloxazol-4-yl-methoxy)cyclohexyloxy]ethyl toluene-4-sulfonate are dissolved in 5 ml of N-methylpyrrolidone, and 200 mg of sodium azide are added. The mixture is stirred at 40° C. for 5 h and, after cooling, taken up in 20 ml of ethyl acetate/20 ml with sat. NaCl solution. The organic phase is dried over sodium sulfate and the solvent is removed under reduced pressure. This gives (1S,3R)-4-[3-(2-azidoethoxy)cyclohexyloxymethyl)-5-methyl-2-m-tolyloxazole as a colorless oil. $C_{20}H_{26}N_4O_3$ (370.46), MS (ESI): 371 (M+H⁺). The crude azide is taken up in 20 ml of methanol and hydrogenated with 50 mg of Pd/C 10% at a hydrogen atmosphere of 1 bar for 3 h. The catalyst is filtered off, giving (1R,3S)-3-[3-(5-methyl-2-m-tolyloxazol-4-ylmethoxy)cyclohexyloxy]ethylamine as a colorless oil. $C_{20}H_{28}N_2O_3$ (244.46), MS (ESI): 345 (M+H⁺).

(1R,3S)—C,C,C-Trifluoro-N-{3-[3-(5-methyl-2-m-tolyloxazol-4-ylmethoxy)cyclohexyloxy]ethyl}-methanesulfonamide

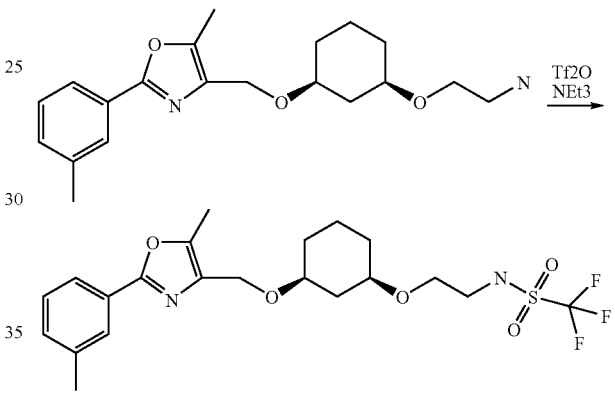

95 mg of (1R,3S)-3-[3-(5-methyl-2-m-tolyloxazol-4-yl-methoxy)cyclohexyloxy]ethylamine are dissolved in 2 ml of dichloromethane, 0.1 ml of triethylamine are added and the mixture is cooled to −78° C. 60 μl of trifluoromethanesulfonic

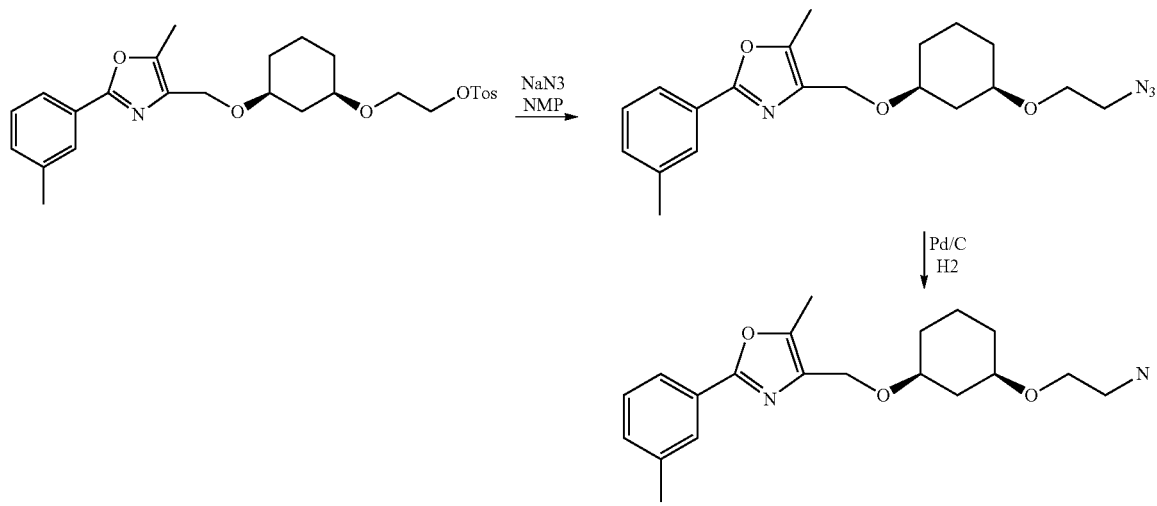

anhydride are added and the mixture is allowed to slowly warm to room temperature. After 3 h, all volatile components were removed under reduced pressure and the residue was taken up in DMF and filtered. The compound is purified by RP-HPLC. This gives (1R,3S)—C,C,C-trifluoro-N-{3-[3-(5-methyl-2-m-tolyloxazol-4-ylmethoxy)cyclohexyloxy]ethyl}-methanesulfonamide as a colorless oil. $C_{21}H_{27}F_3N_2O_5S$ (476.52), MS (ESI): 477 (M+H$^+$).

Example V (1R,3S)-5,7-Difluoro-1-{2-[3-(5-methyl-2-m-tolyloxazol-4-ylmethoxy)cyclohexyloxy]ethyl}-1H-indole-2-carboxylic acid

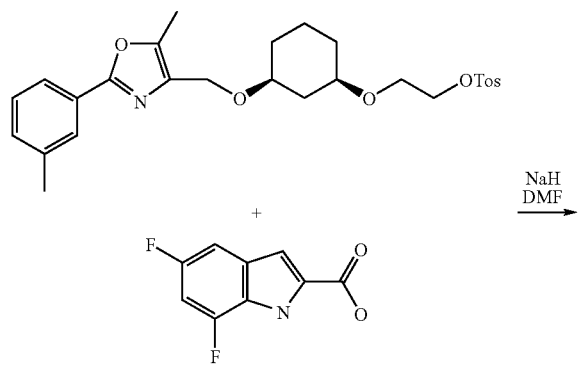

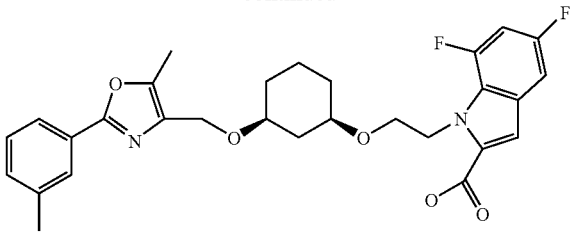

79 mg of 5,7-difluoroindolecarboxylic acid are dissolved in 2 ml of dried DMF, and 34 mg of 60 percent strength sodium hydride suspension are added. After 30 min at room temperature, 100 mg of ((1R,3S)-[3-(5-methyl-2-m-tolyloxazol-4-ylmethoxy)cyclohexyloxy)ethyl toluene-4-sulfonate, dissolved in 2 ml of DMF, are added. The mixture is stirred at 65° C. until the reaction has gone to completion (monitored by LC-MS). 50 μl of TFA are added, the mixture is filtered and the residue is purified by RP-HPLC. This gives 40 mg of (1R,3S)-5,7-difluoro-1-{2-[3-(5-methyl-2-m-tolyloxazol-4-ylmethoxy)cyclohexyloxy]ethyl}-1H-indole-2-carboxylic acid as a colorless oil. $C_{29}H_{30}F_2N_2O_5$ (524.56), MS (ESI): 525 (M+H$^+$).

Example VI (1R,3S)-5-Benzyloxy-1-{2-[3-(5-methyl-2-m-tolyloxazol-4-ylmethoxy)cyclohexyloxy]ethyl}-1H-indole-2-carboxylic acid

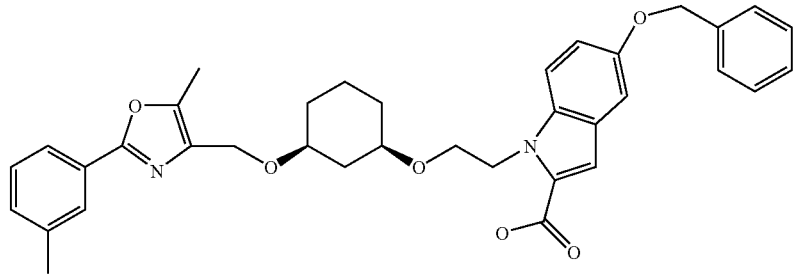

((1R,3S)-[3-(5-Methyl-2-m-tolyloxazol-4-ylmethoxy)cyclohexyloxy]ethyl toluene-4-sulfonate and 5-benzyloxy-1H-indole-2-carboxylic acid give, analogously to Example V, (1R,3S)-5-benzyloxy-1-{2-[3-(5-methyl-2-m-tolyloxazol-4-ylmethoxy)cyclohexyloxy]ethyl}-1H-indole-2-carboxylic acid of molecular weight 594.71 ($C_{36}H_{38}N_2O_6$), MS (ESI): 595 (M+H$^+$).

Example VII (1R,3S)-5-Ethyl-1-{2-[3-(5-methyl-2-m-tolyloxazol-4-ylmethoxy)cyclohexyloxy]ethyl}-1H-indole-2-carboxylic acid ((1R,3S)-[3-(5-Methyl-2-m-tolyloxazol-4-ylmethoxy)cyclohexyloxy]ethyl toluene-4-sulfonate and 5-ethyl-1H-indole-2-carboxylic acid give, analogously to Example V, (1R,3S)-5-ethyl-1-{2-[3-(5-methyl-2-m-tolyloxazol-4-ylmethoxy)cyclohexyloxy]ethyl}-1H-indole-2-carboxylic acid of molecular weight 516.64 ($C_{31}H_{36}N_2O_5$), MS (ESI): 517 (M+H$^+$).

Example VIII (1R,3S)-5-Bromo-1-{2-[3-(5-methyl-2-m-tolyloxazol-4-ylmethoxy)cyclohexyloxy]ethyl}-1H-indole-2-carboxylic acid

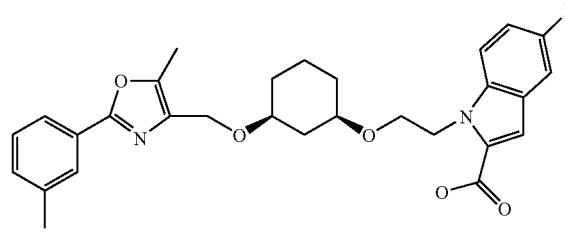

((1R,3S)-[3-(5-Methyl-2-m-tolyloxazol-4-ylmethoxy)cyclohexyloxy]ethyl toluene-4-sulfonate and 5-bromo-1H-indole-2-carboxylic acid give, analogously to Example I, (1R,3S)-5-bromo-1-{2-[3-(5-methyl-2-m-tolyloxazol-4-ylmethoxy)cyclohexyloxy]ethyl}-1H-indole-2-carboxylic acid of molecular weight 567.48 ($C_{29}H_{31}BrN_2O_5$), MS (ESI): 568 (M+H$^+$).

Example IX (1R,3S)-5-(2-Methoxyethoxy)-1-{2-[3-(5-methyl-2-m-tolyloxazol-4-ylmethoxy)cyclohexyloxy]ethyl}-1H-pyrrolo[2,3-c]pyridin-2-carboxylic acid 2-(2-Methoxyethoxy)-4-methyl-5-nitropyridine

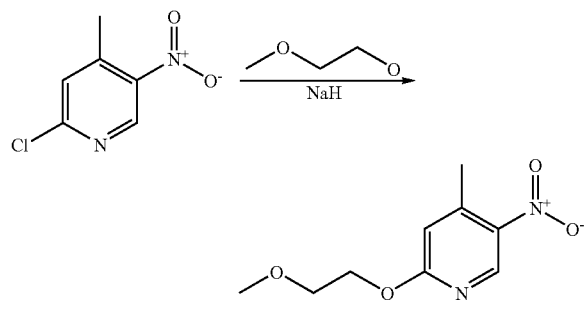

60 percent strength sodium hydride suspension was introduced into 10 ml of ethylene glycol monomethyl ether, and the mixture was stirred until the evolution of hydrogen had ceased. 516 mg of 2-chloro-4-methyl-5-nitropyridine are added, and the mixture is stirred at room temperature until the reaction has gone to completion. 20 ml of water are added, and the mixture is extracted with methyl tert-butyl ether. The organic phase is dried over sodium sulfate and the solvent is removed under reduced pressure. The residue is purified by flash chromatography on silica gel (n-heptane/ethyl acetate=1:3). This gives 2-(2-methoxyethoxy)-4-methyl-5-nitropyridine as a colorless oil. $C_9H_{12}N_2O_4$ (212.21), MS (ESI): 213 (M+H$^+$).

Ethyl 3-[2-(2-methoxyethoxy)-5-nitropyridin-4-yl]-2-oxopropionate potassium salt

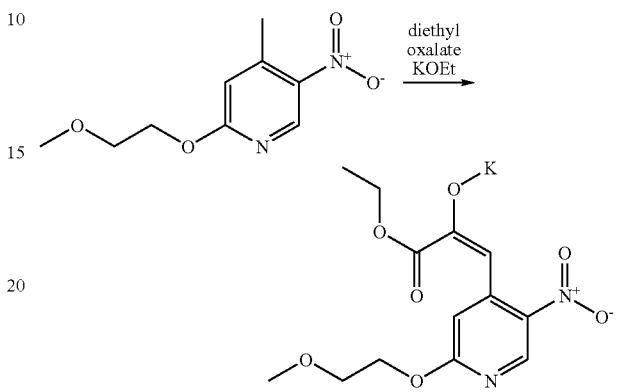

1.86 g of potassium are initially charged in 120 ml of dry diethyl ether, and 15 ml of EtOH are added slowly. The mixture is cooled to 0° C. 5 g of 2-(2-methoxyethoxy)-4-methyl-5-nitropyridine are dissolved in 15 ml of dry ether and 3 ml of EtOH and added. 27.5 g of diethyl oxalate were dissolved in 100 ml of toluene and, at 0° C., added dropwise over a period of 45 min. The mixture is stirred at room temperature for 24 h. The precipitate is allowed to settle, the mixture is filtered and the precipitate is washed with ether/n-heptane 1:1. The precipitate is dried under high vacuum. This gives ethyl 3-[2-(2-methoxyethoxy)-5-nitropyridin-4-yl]-2-oxopropionate potassium salt as a red solid. (LC-MS protonate form) $C_{13}H_{16}N_2O_7$ (312.28), MS (ESI): 313 (M+H$^+$).

Ethyl 5-(2-methoxyethoxy)-1H-pyrrolo[2,3-c]pyridine-2-carboxylate

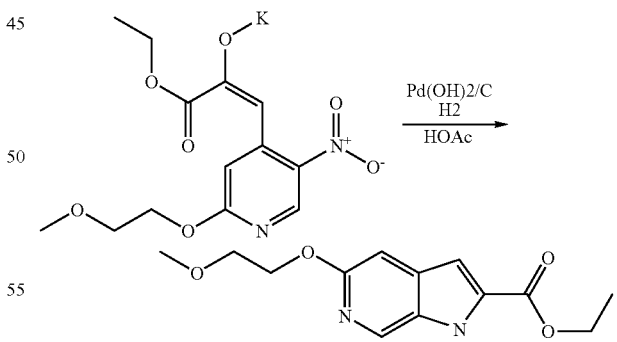

3.5 g of dried ethyl 3-[2-(2-methoxyethoxy)-5-nitropyridin-4-yl]-2-oxopropionate potassium salt are dissolved in 50 ml of MeOH, and 2 ml of acetic acid are added. After the addition of 500 mg of palladium hydroxide/C 20%, the mixture is stirred under 1 atm of hydrogen. After 5 h, a further 200 mg of catalyst and 0.75 ml of trifluoroethanol are added. After a further 3 h, all volatile components are removed under reduced pressure and 20 ml of sat. sodium bicarbonate solution are added and the mixture is extracted with ethyl acetate.

The organic phase is dried over sodium sulfate and the solvent is removed under reduced pressure. The residue is purified by flash chromatography on silica gel (n-heptane/ethyl acetate=1:2). This gives ethyl 5-(2-methoxyethoxy)-1H-pyrrolo[2,3-c]pyridine-2-carboxylate as a yellowish solid. $C_{13}H_{16}N_2O_4$ (264.28), MS (ESI): 265 (M+H⁺).

Ethyl 5-(2-methoxyethoxy)-1-{2-[3-(5-methyl-2-m-tolyloxazol-4-ylmethoxy)cyclohexyloxy]ethyl}-1H-pyrrolo[2,3-c]pyridine-2-carboxylate

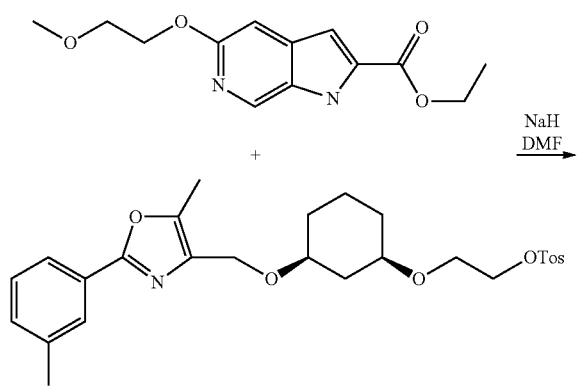

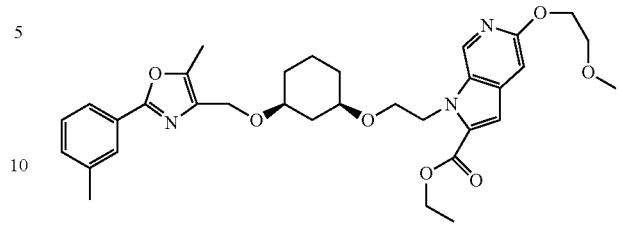

66 mg of ethyl 5-(2-methoxyethoxy)-1H-pyrrolo[2,3-c]pyridine-2-carboxylate are dissolved in 2 ml of dry DMF, and 12 mg of 60 percent strength sodium hydride suspension are added. After 30 min at room temperature, 100 mg of ((1R, 3S)-[3-(5-methyl-2-m-tolyloxazol-4-ylmethoxy)cyclohexyloxy]ethyl toluene-4-sulfonate ((1R,3S)-[3-(5-methyl-2-m-tolyloxazol-4-ylmethoxy)cyclohexyloxy]ethyl toluene-4-sulfonate in 2 ml of DMF are added. The mixture is stirred at 40° C. until the reaction has gone to completion (monitored by LC-MS). After cooling, the mixture is diluted with sat. NaCl solution and ethyl acetate. The organic phase is dried over sodium sulfate and the solvent is removed under reduced pressure. The residue is purified by flash chromatography on silica gel (n-heptane/ethyl acetate=1:2). This gives ethyl 5-(2-methoxyethoxy)-1-{2-[3-(5-methyl-2-m-tolyloxazol-4-ylmethoxy)cyclohexyloxy]ethyl}-1H-pyrrolo[2,3-c]pyridine-2-carboxylate as a yellowish solid. $C_{33}H_{41}N_3O_7$ (591.71), MS (ESI): 592 (M+H⁺).

(1R,3S)-5-(2-Methoxyethoxy)-1-{2-[3-(5-methyl-2-m-tolyloxazol-4-yl-methoxy)cyclohexyloxy]ethyl}-1H-pyrrolo[2,3-c]pyridine-2-carboxylic acid

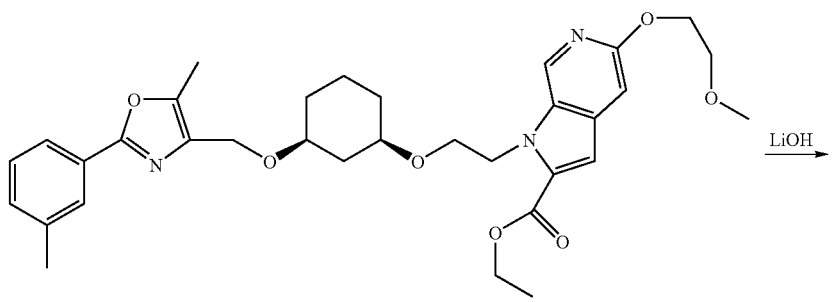

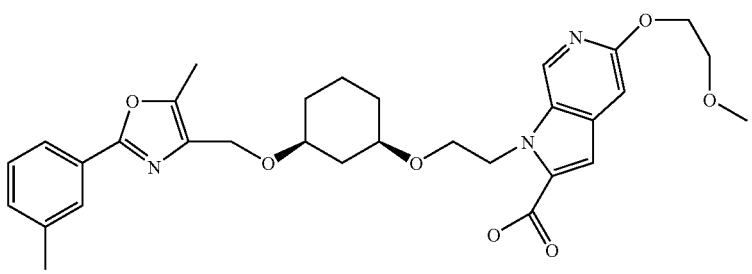

60 mg of ethyl 5-(2-methoxyethoxy)-1-{2-[3-(5-methyl-2-m-tolyloxazol-4-ylmethoxy)cyclohexyloxy]ethyl}-1H-pyrrolo[2,3-c]pyridine-2-carboxylate are dissolved in 2 ml of THF/methanol 3:1, and 0.15 ml of a 1 N lithium hydroxide solution is added. The mixture is stirred at room temperature for 24 h. All volatile components are removed under reduced pressure, the residue is taken up in DMF/acetonitrile, 70 µl of TFA are added and the mixture is filtered and purified by RP-HPLC. This gives 14 mg of (1R,3S)-5-(2-methoxyethoxy)-1-{2-[3-(5-methyl-2-m-tolyloxazol-4-ylmethoxy)cyclohexyloxy]ethyl}-1H-pyrrolo[2,3-c]pyridine-2-carboxylic acid as a colorless oil. $C_{31}H_{37}N_3O_7$ (563.66), MS (ESI): 564 (M+H$^+$).

Example X (1R,3S)-5-Cyano-1-{2-[3-(5-methyl-2-m-tolyloxazol-4-ylmethoxy)cyclohexyloxy]ethyl}-1H-indole-2-carboxylic acid

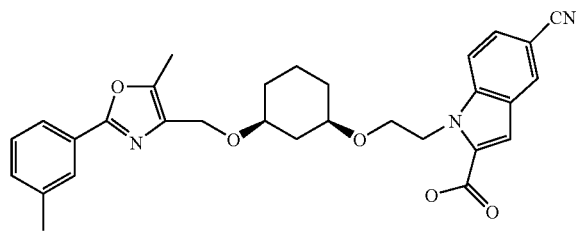

((1R,3S)-[3-(5-Methyl-2-m-tolyloxazol-4-ylmethoxy)cyclohexyloxy]ethyl toluene-4-sulfonate and ethyl 5-cyano-1H-indole-2-carboxylate give, analogously to Example IX, (1R,3S)-5-cyano-1-{2-[3-(5-methyl-2-m-tolyloxazol-4-ylmethoxy)cyclohexyloxy]ethyl}-1H-indole-2-carboxylic acid of molecular weight 513.60 ($C_{30}H_{31}N_3O_5$), MS (ESI): 514 (M+H$^+$).

Example XI (1R,3S)-6-Methoxy-1-{2-[3-(5-methyl-2-m-tolyloxazol-4-ylmethoxy)cyclohexyloxy]ethyl}-1H-indole-2-carboxylic acid

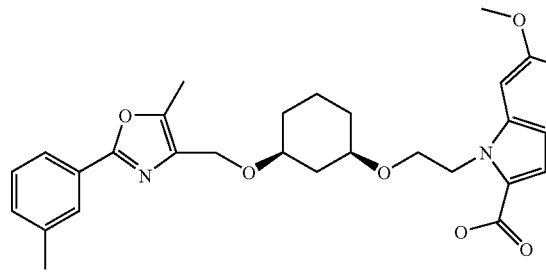

((1R,3S)-[3-(5-Methyl-2-m-tolyloxazol-4-ylmethoxy)cyclohexyloxy]ethyl toluene-4-sulfonate and methyl 6-methoxy-1H-indole-2-carboxylate give, analogously to Example IX, (1R,3S)-6-methoxy-1-{2-[3-(5-methyl-2-m-tolyloxazol-4-ylmethoxy)cyclohexyloxy]ethyl}-1H-indole-2-carboxylic acid of molecular weight 518.62 ($C_{30}H_{34}N_2O_6$), MS (ESI): 519 (M+H$^+$).

Example XII (1R,3S)-5,6-Dimethoxy-1-{2-[3-(5-methyl-2-m-tolyloxazol-4-ylmethoxy)cyclohexyloxy]ethyl}-1H-indole-2-carboxylic acid

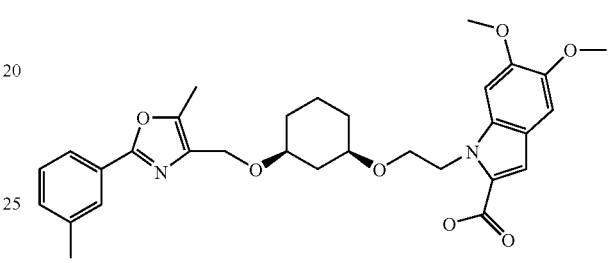

((1R,3S)-[3-(5-Methyl-2-m-tolyloxazol-4-ylmethoxy)cyclohexyloxy]ethyl toluene-4-sulfonate and ethyl 5,6-dimethoxy-1H-indole-2-carboxylate give, analogously to Example IX, (1R,3S)-5,6-dimethoxy-1-{2-[3-(5-methyl-2-m-tolyloxazol-4-ylmethoxy)cyclohexyloxy]ethyl}-1H-indole-2-carboxylic acid of molecular weight 548.64 ($C_{31}H_{36}N_2O_7$), MS (ESI): 549 (M+H$^+$).

Example XIII (1R,3S)-5-Methanesulfonyl-1-{2-[3-(5-methyl-2-m-tolyloxazol-4-ylmethoxy)cyclohexyloxy]ethyl}-1H-indole-2-carboxylic acid

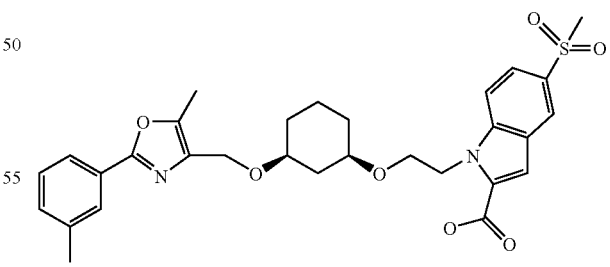

((1R,3S)-[3-(5-Methyl-2-m-tolyloxazol-4-ylmethoxy)cyclohexyloxy]ethyl toluene-4-sulfonate and methyl 5-methanesulfonyl-1H-indole-2-carboxylate give, analogously to Example IX, (1R,3S)-5-methanesulfonyl-1-{2-[3-(5-methyl-2-m-tolyloxazol-4-ylmethoxy)cyclohexyloxy]ethyl}-1H-indole-2-carboxylic acid of molecular weight 566.68 ($C_{30}H_{34}N_2O_7S$), MS (ESI): 567 (M+H$^+$).

Example XIV

(1R,3S)-2-Methyl-6-{2-[3-(5-methyl-2-m-tolyloxazol-4-ylmethoxy)cyclohexyloxy]ethoxy}benzoic acid

Ethyl (1R,3S)-2-methyl-6-{2-[3-(5-methyl-2-m-tolyloxazol-4-ylmethoxy)cyclohexyloxy]ethoxy}benzoate

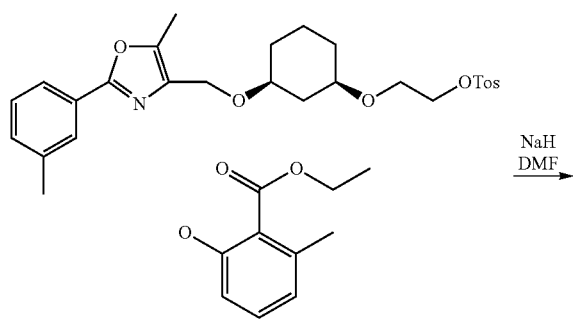

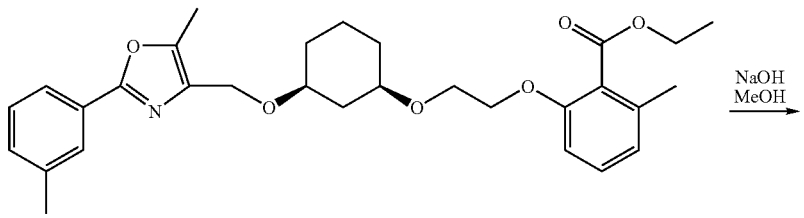

90 mg of ethyl 2-hydroxy-6-methylbenzoate are dissolved in 2 ml of dry DMF, and 23 mg of a 60 percent strength sodium hydride suspension are added. After 30 min at room temperature, 100 mg of ((1R,3S)-[3-(5-methyl-2-m-tolyloxazol-4-ylmethoxy)cyclohexyloxy]ethyl toluene-4-sulfonate in 2 ml of DMF are added. The mixture is stirred at 40° C. until the reaction has gone to completion (monitored by LC-MS). After cooling, the mixture is diluted with sat. NaCl solution and ethyl acetate. The organic phase is dried over sodium sulfate and the solvent is removed under reduced pressure. This gives ethyl (1R,3S)-2-methyl-6-{2-[3-(5-methyl-2-m-tolyloxazol-4-ylmethoxy)cyclohexyloxy]ethoxy}benzoate as a yellowish oil. $C_{30}H_{37}NO_6$ (507.63), MS (ESI): 508 (M+H$^+$).

(1R,3S)-2-Methyl-6-{2-[3-(5-methyl-2-m-tolyloxazol-4-ylmethoxy)cyclohexyloxy]ethoxy}benzoic acid

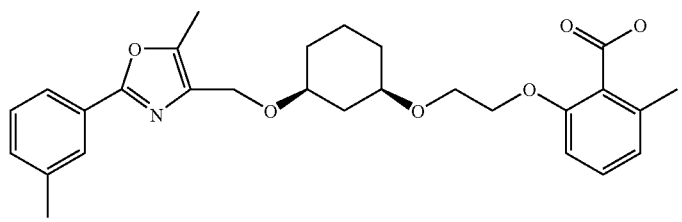

Unpurified ethyl (1R,3S)-2-methyl-6-{2-[3-(5-methyl-2-m-tolyloxazol-4-ylmethoxy)cyclohexyloxy]ethoxy}benzoate are dissolved in 3 ml of methanol, and 0.25 ml of a 5 N sodium hydroxide solution are added. The mixture is stirred at 60° C. for 8 h and at 80° C. for 12 h. After cooling, the mixture is taken up in 2N HCl/ethyl acetate, the organic phase is dried over sodium sulfate and the solvent is removed under reduced pressure. The residue is purified by RP-HPLC. This gives (1R,3S)-2-methyl-6-{2-[3-(5-methyl-2-m-tolyloxazol-4-ylmethoxy)cyclohexyloxy]ethoxy)benzoic acid as a colorless oil. $C_{28}H_{33}NO_6$ (479.58), MS (ESI). 480 (M+H$^+$).

Example XV (1R,3S)-2-{2-[3-(5-Methyl-2-m-tolyloxazol-4-yl-methoxy)cyclohexyloxy]-ethoxy}benzoic acid

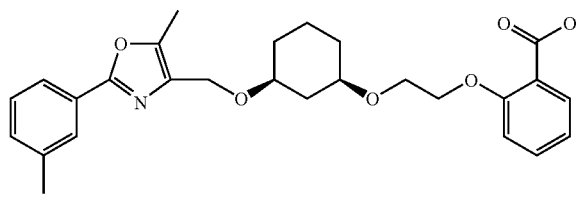

((1R,3S)-[3-(5-Methyl-2-m-tolyloxazol-4-ylmethoxy)cyclohexyloxy]ethyl toluene-4-sulfonate and methyl 2-hydroxybenzoate give, analogously to Example XIV, (1R,3S)-2-{2-[3-(5-methyl-2-m-tolyloxazol-4-ylmethoxy)cyclohexyloxy]ethoxy}benzoic acid of molecular weight 465.55 ($C_{27}H_{31}NO_6$), MS (ESI): 466 (M+H$^+$).

Example XVI (1R,3S)-2-Fluoro-6-{2-[3-(5-methyl-2-m-tolyloxazol-4-ylmethoxy)cyclohexyloxy]ethoxy}benzoic acid

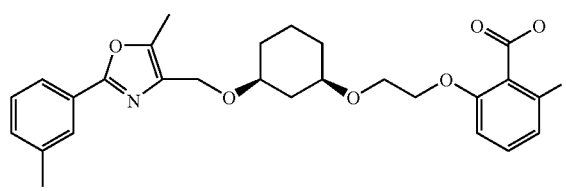

((1R,3S)-[3-(5-Methyl-2-m-tolyloxazol-4-ylmethoxy)cyclohexyloxy]ethyl toluene-4-sulfonate and methyl 2-fluoro-6-hydroxybenzoate give, analogously to Example XIV, (1R,3S)-2-fluoro-6-{2-[3-(5-methyl-2-m-tolyloxazol-4-ylmethoxy)cyclohexyloxy]ethoxy}benzoic acid of molecular weight 483.54 ($C_{27}H_{30}FNO_6$), MS (ESI): 484 (M+H$^+$).

Example XVII (1R,3S)-2-Fluoro-6-{2-[3-(5-methyl-2-m-tolyloxazol-4-ylmethoxy)cyclohexyloxy]ethoxy}benzoic acid

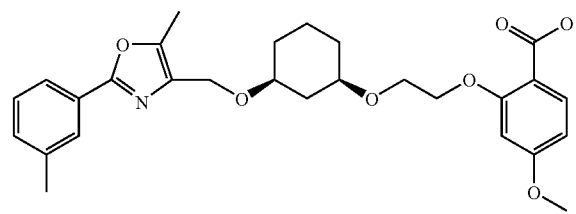

((1R,3S)-[3-(5-Methyl-2-m-tolyloxazol-4-ylmethoxy)cyclohexyloxy]ethyl toluene-4-sulfonate and methyl 4-methoxy-2-hydroxybenzoate give, analogously to Example XIV, (1R,3S)-2-fluoro-6-{2-[3-(5-methyl-2-m-tolyloxazol-4-ylmethoxy)cyclohexyloxy]ethoxy}benzoic acid of molecular weight 495.58 ($C_{28}H_{33}NO_7$), MS (ESI): 496 (M+H$^+$).

Example XVIII (1R,3S)-4-isobutoxy-2-{2-[3-(5-methyl-2-m-tolyloxazol-4-ylmethoxy)cyclohexyloxy]ethoxy}benzoic acid

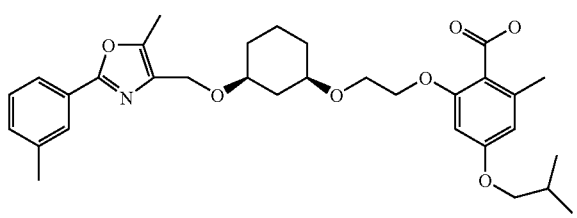

((1R,3S)-[3-(5-Methyl-2-m-tolyloxazol-4-ylmethoxy)cyclohexyloxy]ethyl toluene-4-sulfonate and ethyl 4-isopropoxy-2-hydroxy-6-methylbenzoate give, analogously to Example XIV, (1R,3S)-4-isobutoxy-2-{2-[3-(5-methyl-2-m-tolyloxazol-4-ylmethoxy)cyclohexyloxy]ethoxy}benzoic acid of molecular weight 551.69 ($C_{32}H_{41}NO_7$), MS (ESI): 552 (M+H$^+$).

Example XIX (1R,3S)-4-Benzyloxy-2-{2-[3-(5-methyl-2-m-tolyloxazol-4-ylmethoxy)cyclohexyloxy]ethoxy}benzoic acid

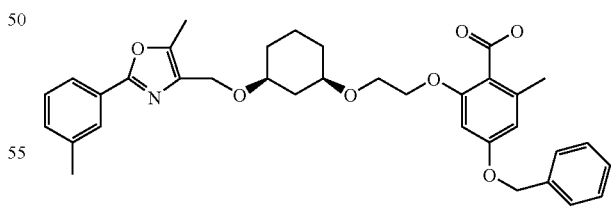

((1R,3S)-[3-(5-Methyl-2-m-tolyloxazol-4-ylmethoxy)cyclohexyloxy]ethyl toluene-4-sulfonate and ethyl 4-benzyloxy-2-hydroxy-6-methylbenzoate give, analogously to Example XIV, (1R,3S)-4-benzyloxy-2-{2-[3-(5-methyl-2-m-tolyloxazol-4-ylmethoxy)cyclohexyloxy]ethoxy}benzoic acid of molecular weight 585.70 ($C_{35}H_{39}NO_7$), MS (ESI): 586 (M+H$^+$).

Example XX (1S,3R)-5-Methyl-4-{3-[2-(2-nitrophenoxy)ethoxy]cyclohexyloxymethyl}-2-m-tolyloxazole

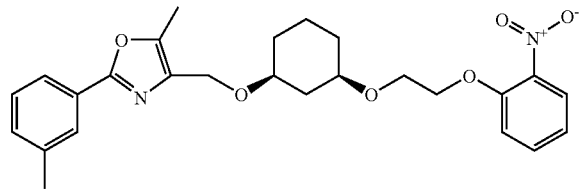

((1R,3S)-[3-(5-Methyl-2-m-tolyloxazol-4-ylmethoxy)cyclohexyloxy]ethyl toluene-4-sulfonate and 2-hydroxynitrobenzene give, analogously to Example XIV, (1S,3R)-5-methyl-4-{3-[2-(2-nitrophenoxy)ethoxy] cyclohexyloxymethyl}-2-m-tolyloxazole of molecular weight 466.54 ($C_{26}H_{30}N_2O_6$), MS (ESI): 467 (M+H$^+$).

Example XXI (1S,3R)-5-Methyl-4-{3-[2-(3-methyl-2-nitrophenoxy)ethoxy]cyclohexyloxymethyl}-2-m-tolyloxazole

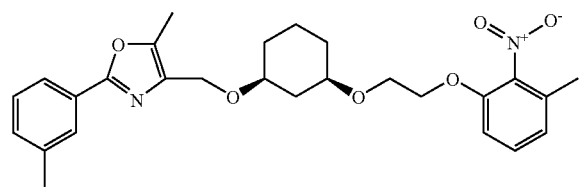

((1R,3S)-[3-(5-Methyl-2-m-tolyloxazol-4-ylmethoxy)cyclohexyloxy]ethyl toluene-4-sulfonate and 6-methyl-2-hydroxynitrobenzene give, analogously to Example XIV, (1S,3R)-5-methyl-4-{3-[2-(3-methyl-2-nitrophenoxy)ethoxy]cyclohexyloxymethyl}-2-m-tolyloxazole of molecular weight 480.57 ($C_{27}H_{32}N_2O_6$), MS (ESI): 481 (M+H$^+$).

Example XXII (1R,3S)-2-{2-[3-(5-Methyl-2-m-tolyloxazol-4-ylmethoxy)cyclohexyloxy]ethoxy}phenylboronic acid (1S,3R)-5-Methyl-4-(3-{2-[2-(4,4,5,5-tetramethyl-[1,3,2]dioxaborolan-2-yl)phenoxy]ethoxy}cyclohexyloxymethyl)-2-m-tolyloxazole

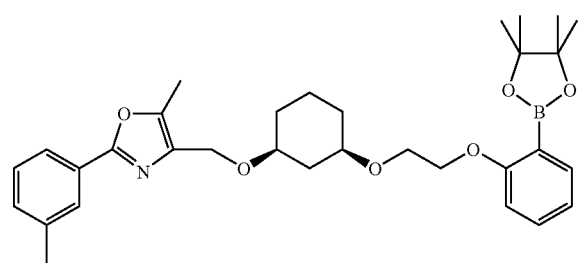

((1R,3S)-[3-(5-Methyl-2-m-tolyloxazol-4-ylmethoxy)cyclohexyloxy]ethyl toluene-4-sulfonate and 2-(4,4,5,5-tetramethyl-[1,3,2]dioxaborolan-2-yl)phenol give, analogously to Example XIV, (1S,3R)-5-methyl-4-(3-{2-[2-(4,4,5,5-tetramethyl-[1,3,2]dioxaborolan-2-yl)phenoxy]ethoxy}cyclohexyloxymethyl)-2-m-tolyloxazole of molecular weight 547.51 ($C_{32}H_{42}BNO_6$), MS (ESI): 548 (M+H$^+$).

(1R,3S)-2-{2-[3-(5-Methyl-2-m-tolyloxazol-4-ylmethoxy)cyclohexyloxy]ethoxy}phenylboronic acid

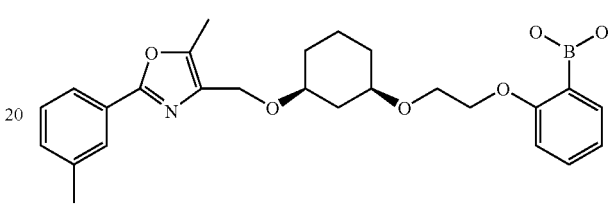

Unpurified (1S,3R)-5-methyl-4-(3-{2-[2-(4,4,5,5-tetramethyl-[1,3,2]dioxaborolan-2-yl)phenoxy]ethoxy}cyclohexyloxymethyl)-2-m-tolyloxazole is taken up in 6 ml of THF, and 0.75 ml of 1N HCl is added. After 3 h of stirring at room temperature, the solvent is evaporated and the residue is taken up in DMF then purified by RP-HPLC. This gives (1R,3S)-2-{2-[3-(5-methyl-2-m-tolyloxazol-4-ylmethoxy)cyclohexyloxy]ethoxy}phenylboronic acid as a colorless oil. 465.36 ($C_{26}H_{32}BNO_6$), MS (ESI): 466 (M+H$^+$).

Example XXIII (1R,3S)-3-{2-[3-(5-Methyl-2-m-tolyloxazol-4-ylmethoxy)cyclohexyloxy]ethoxy}-5-trifluoromethylthiophene-2-carboxylic acid

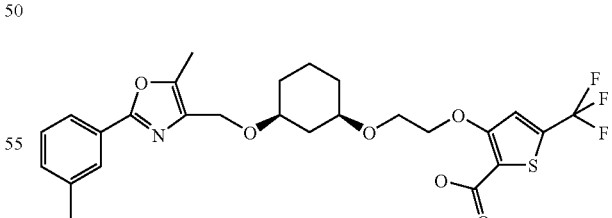

((1R,3S)-[3-(5-Methyl-2-m-tolyloxazol-4-ylmethoxy)cyclohexyloxy]ethyl toluene-4-sulfonate and methyl 3-hydroxy-5-trifluoromethylthiophene-2-carboxylate give, analogously to Example XIV, (1R,3S)-3-{2-[3-(5-methyl-2-m-tolyloxazol-4-ylmethoxy)cyclohexyloxy]ethoxy}-5-trifluoromethylthiophene-2-carboxylic acid of molecular weight 539.58 ($C_{26}H_{28}F_3NO_6S$), MS (ESI): 540 (M+H$^+$).

Example XXIV (1R,3S)—C,C,C-Trifluoro-N-{3-[3-(5-methyl-2-m-tolyloxazol-4-ylmethoxy)cyclohexyloxymethyl]phenyl}methanesulfonamide (1S,3R)-5-Methyl-4-[3-(3-nitrobenzyloxy)cyclohexyloxymethyl]-2-m-tolyloxazole

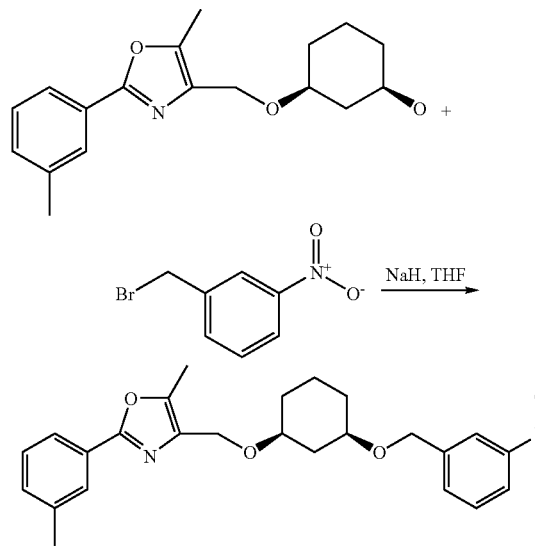

530 µl of 1M NaHMDS in THF are added to 150 mg of 3-((1R,3S)-cis-5-methyl-2-m-tolyloxazol-4-ylmethoxy)cyclohexanol in 3 ml of THF, and the mixture is stirred at RT for 10 min. 121 mg of 3-nitrobenzyl bromide are added, and the mixture is stirred at 60° C. for 5 h. After addition of further 3-nitrobenzyl bromide the mixture is stirred overnight. The mixture is taken up in sat. NaCl solution/ethyl acetate. The org. phase is dried over sodium sulfate and evaporated. The residue is purified by chromatography on silica gel. This gives (1S,3R)-5-methyl-4-[3-(3-nitrobenzyloxy)cyclohexyloxymethyl]-2-m-tolyloxazole as a colorless oil of molecular weight 436.51 ($C_{25}H_{28}N_2O_5$), MS (ESI): 437 (M+H$^+$).

(1R,3S)-3-[3-(5-Methyl-2-m-tolyloxazol-4-ylmethoxy)cyclohexyloxymethyl]phenylamine

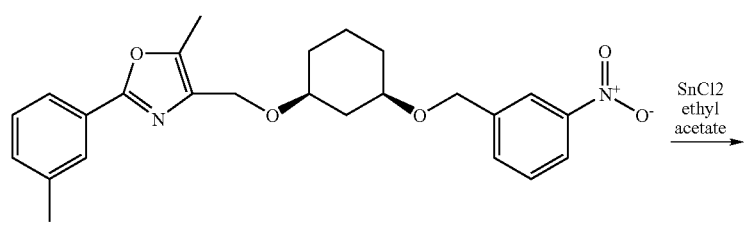

400 mg of tin(II) chloride dihydrate are added to 150 mg of (1S,3R)-5-methyl-4-[3-(3-nitrobenzyloxy)cyclohexyloxymethyl]-2-m-tolyloxazole in 24 ml of ethyl acetate, and the mixture is stirred at room temperature. After every 8 h, 400 mg of tin(II) chloride dihydrate are added, until the reaction has gone to completion. The mixture is diluted with ethyl acetate and washed with water. The org. phase is dried over sodium sulfate and evaporated. The residue is used for the next reaction without purification. This gives (1R,3S)-3-[3-(5-methyl-2-m-tolyloxazol-4-ylmethoxy)cyclohexyloxymethyl]phenylamine as a colorless oil of molecular weight 406.53 ($C_{25}H_{30}N_2O_3$), MS (ESI): 407 (M+H$^+$).

(1R,3S)—C,C,C-Trifluoro-N-{3-[3-(5-methyl-2-m-tolyloxazol-4-ylmethoxy)cyclohexyloxymethyl]phenyl}methanesulfonamide

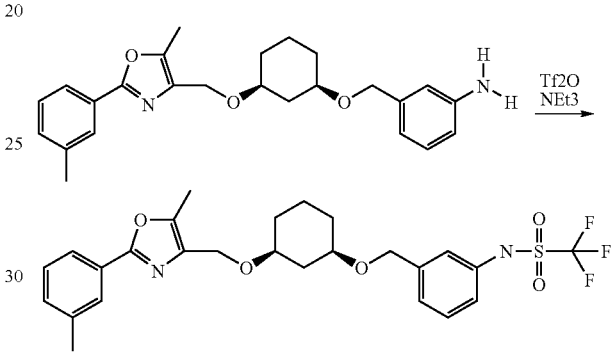

55 mg of (1R,3S)-3-[3-(5-methyl-2-m-tolyloxazol-4-ylmethoxy)cyclohexyloxymethyl]phenylamine are dissolved in 2 ml of dichloromethane and cooled to −78° C. 100 µl of triethylamine and then 42 µl of trifluoromethanesulfonic anhydride are added. After 1 h, 200 µl of water are added and the mixture is allowed to warm to room temperature. The mixture is diluted with dichloromethane and washed with 1 NHCL and sat. NaCl solution. The org. phase is dried over sodium sulphate and evaporated. The residue is purified by RP-HPLC. This gives (1R,3S)—C,C,C-trifluoro-N-{3-[3-(5-methyl-2-m-tolyloxazol-4-ylmethoxym-

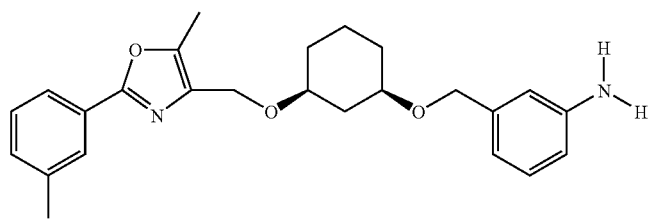

ethyl]phenyl}methanesulfonamide as a colorless oil of molecular weight 538.59 ($C_{26}H_{29}F_3N_2O_5S$), MS (ESI): 539 (M+H$^+$).

Example XXV (1R,3S)-2-[3-(5-Methyl-2-m-tolyloxazol-4-yl-methoxy)cyclohexyloxymethyl]benzeneboronic acid (1S,3R)-5-Methyl-4-{3-[2-(4,4,5,5-tetramethyl-[1,3,2]dioxaborolan-2-yl)benzyloxy]cyclohexyloxymethyl}-2-m-tolyloxazole

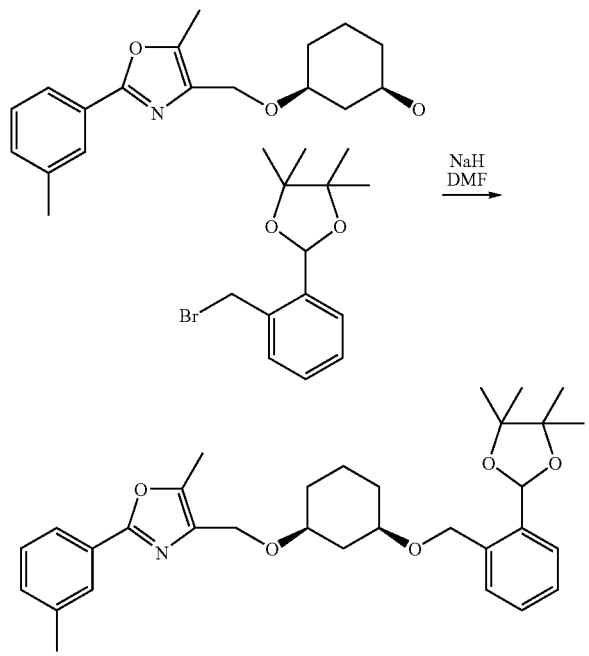

60 mg (1.6 mmol) of NaH were added to 300 mg of 3-((1R,3S)-cis-5-methyl-2-m-tolyloxazol-4-ylmethoxy)cyclohexanol in 5 ml of DMF, and the mixture is stirred at RT for 10 min. After addition of 335 mg of 2-(2-bromomethylphenyl)-4,4,5,5-tetramethyl-[1,3,2]dioxaborolan, the mixture is stirred until maximum conversion has been achieved and quenched with MeOH. The mixture is taken up in sat. NaCl solution/ethyl acetate, the organic phase is dried over sodium sulfate and filtered and the solvent is removed under reduced pressure. The residue is purified by flash chromatography on silica gel (n-heptane/ethyl acetate=1:1). This gives (1S,3R)-5-methyl-4-{3-[2-(4,4,5,5-tetramethyl-[1,3,2]dioxaborolan-2-yl)benzyloxy]cyclohexyloxymethyl}-2-m-tolyloxazole as a colorless oil. $C_{31}H_{40}BNO_5$ (517.48), MS (ESI): 518 (M+H$^+$).

(1R,3S)-2-[3-(5-Methyl-2-m-tolyloxazol-4-yl-methoxy)cyclohexyloxymethyl]benzeneboronic acid

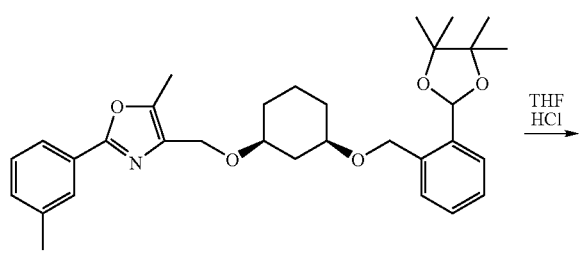

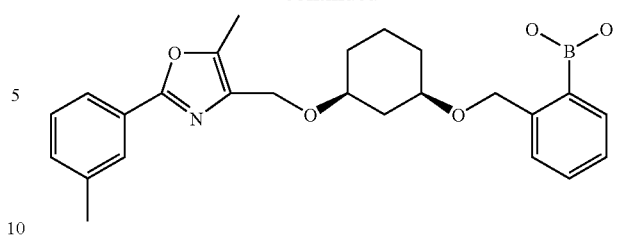

1 ml of 1 N HCl is added to 300 mg of (1S,3R)-5-methyl-4-{3-[2-(4,4,5,5-tetramethyl-[1,3,2]dioxaborolan-2-yl)benzyloxy]cyclohexyloxymethyl}-2-m-tolyloxazole in 5 ml of THF, and the mixture is stirred at RT until the reaction has gone to completion. The solvent is removed under reduced pressure and the compound is purified by RP-HPLC. This gives (1R,3S)-2-[3-(5-methyl-2-m-tolyloxazol-4-ylmethoxy)cyclohexyloxymethyl]benzeneboronic acid as a colorless oil. $C_{25}H_{30}BNO_5$ (435.33), MS (ESI): 436 (M+H$^+$).

Example XXVI

1-[(1S,3R)/(1R,3S)-3-(5-Methyl-2-p-tolyloxazol-4-ylmethoxy)cyclohexylmethyl]-1H-indole-2-carboxylic acid cis-3-Hydroxymethylcyclohexanol

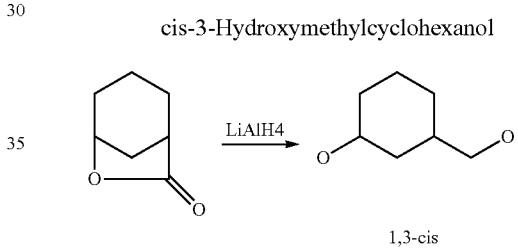

10 g of 6-oxabicyclo[3.2.1]octan-7-one are dissolved in 300 ml of tetrahydrofuran, and 160 ml of a 1M solution of lithium aluminum hydride in tetrahydrofuran are added with ice cooling. After 30 minutes of stirring at room temperature, saturated ammonium chloride solution is added and the pH is adjusted to neutral by addition of a 5% strength solution of citric acid. The tetrahydrofuran is removed under reduced pressure and the residue is extracted three times with in each case 150 ml of ethyl acetate. The combined organic phases are dried over MgSO4 and the solvent is then removed under reduced pressure. This gives 10.5 g of (1S,3R)/(1R,3S)-3-hydroxymethylcyclohexanol as a colorless oil. C7H14O2 (130.13), Rf(ethyl acetate)=0.14.

(1S,3R)/(1R,3S)-3-(tert-Butyldiphenylsilanyloxymethyl)cyclohexanol

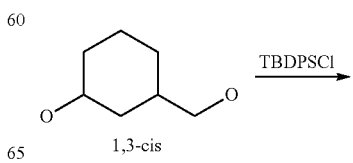

-continued

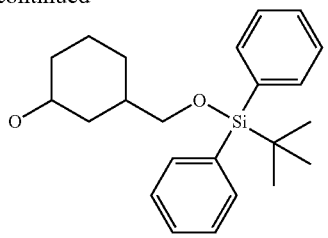

10.5 g of (1S,3R)/(1R,3S)-3-hydroxymethylcyclohexanol are dissolved in 300 ml of dimethylformamide, and 23 ml of tert-butyldiphenylsilanyl chloride, 8.0 g of imidazole and 200 mg of dimethylaminopyridine are added. The mixture is stirred at room temperature for 12 hours. The dimethylformamide is removed under reduced pressure and the residue is dissolved in 300 ml of ethyl acetate and washed five times with in each case 100 ml of water. The organic phase is dried over MgSO4 and the solvent is then removed under reduced pressure. This gives 27.0 g of (1S,3R)/(1R,3S)-3-(tert-butyldiphenylsilanyloxymethyl)cyclohexanol as an oil. C23H32O2Si (368.6), Rf(n-heptane:ethyl acetate=1:1)=0.42.

4-[(1S,3R)/(1R,3S)-3-(tert-Butyldiphenylsilanyloxymethyl)cyclohexyloxymethyl]-5-methyl-2-p-tolyloxazole

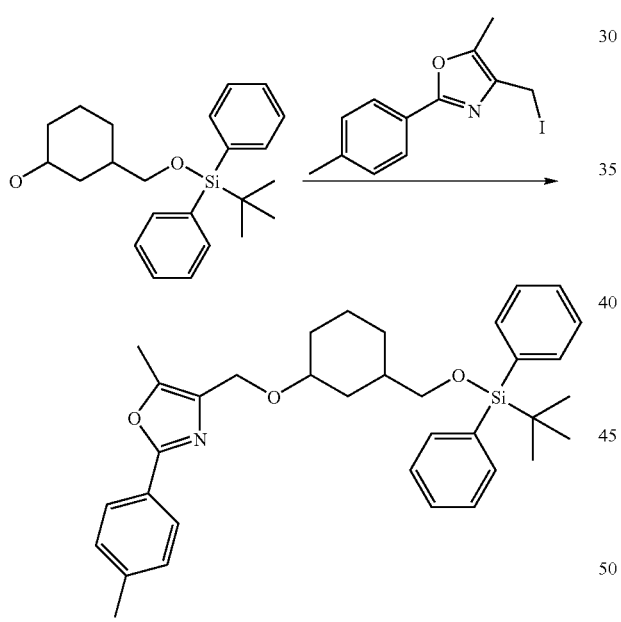

6.4 g of (1S,3R)/(1R,3S)-3-(tert-butyldiphenylsilanyloxymethyl)cyclohexanol and 6.5 g of 4-iodomethyl-5-methyl-2-p-tolyloxazole are dissolved in 200 ml of dimethylformamide, and 1 g of sodium hydride (60% strength suspension in mineral oil) is added. After 1 hour of stirring at room temperature, another 2 g of sodium hydride and 5 g of 4-iodomethyl-5-methyl-2-p-tolyloxazole are added. After 4 hours of stirring at room temperature, the reaction mixture is diluted by addition of 400 ml of ethyl acetate and washed five times with in each case 200 ml of water. The organic phase is dried over MgSO4 and the solvent is then removed under reduced pressure. The residue is purified on silica gel using the mobile phase n-heptane:ethyl acetate=10:1. This gives 6.8 g of 4-[(1S,3R)/(1R,3S)-3-(tert-butyldiphenylsilanyloxymethyl)cyclohexyloxymethyl]-5-methyl-2-p-tolyloxazole as an oil. C35H43NO3Si (553.28), Rf(n=heptane:ethyl acetate=2:1)=0.50.

[(1S,3R)/(1R,3S)-3-(5-Methyl-2-p-tolyloxazol-4-ylmethoxy)cyclohexyl]methanol

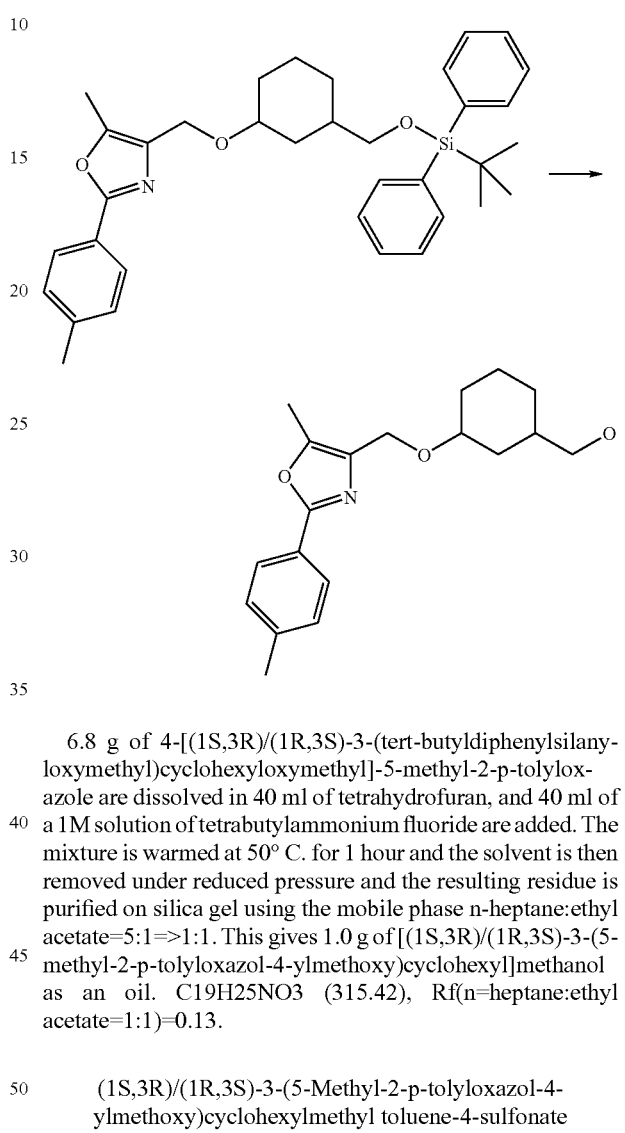

6.8 g of 4-[(1S,3R)/(1R,3S)-3-(tert-butyldiphenylsilanyloxymethyl)cyclohexyloxymethyl]-5-methyl-2-p-tolyloxazole are dissolved in 40 ml of tetrahydrofuran, and 40 ml of a 1M solution of tetrabutylammonium fluoride are added. The mixture is warmed at 50° C. for 1 hour and the solvent is then removed under reduced pressure and the resulting residue is purified on silica gel using the mobile phase n-heptane:ethyl acetate=5:1=>1:1. This gives 1.0 g of [(1S,3R)/(1R,3S)-3-(5-methyl-2-p-tolyloxazol-4-ylmethoxy)cyclohexyl]methanol as an oil. C19H25NO3 (315.42), Rf(n=heptane:ethyl acetate=1:1)=0.13.

(1S,3R)/(1R,3S)-3-(5-Methyl-2-p-tolyloxazol-4-ylmethoxy)cyclohexylmethyl toluene-4-sulfonate

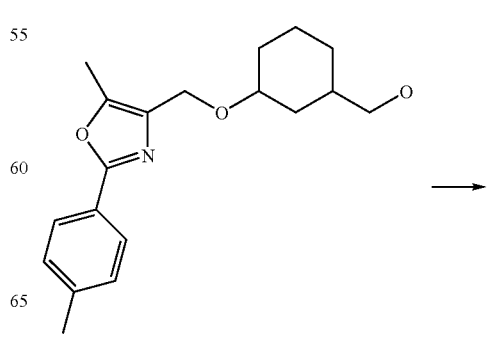

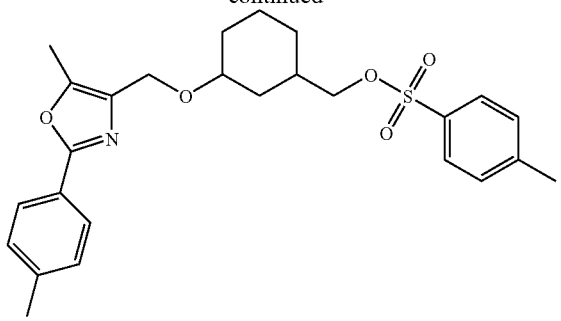

1 g of [(1S,3R)/(1R,3S)-3-(5-methyl-2-p-tolyloxazol-4-ylmethoxy)cyclohexyl]methanol together with 730 mg of p-toluenesulfonyl chloride, 0.7 ml of triethylamine and 50 mg of a dimethylaminopyridine are dissolved in 20 ml of dichloromethane and stirred at room temperature for 24 h. The mixture is washed with water and saturated sodium bicarbonate solution, the organic phase is dried over MgSO4 and the solvent is then removed under reduced pressure. This gives 1.5 g of (1S,3R)/(1R,3S)-3-(5-methyl-2-p-tolyloxazol-4-ylmethoxy)cyclohexylmethyl toluene-4-sulfonate as a brown oil which is reacted further without purification. C26H31NO5S (469.60), Rf(n=heptane:ethyl acetate=1:1) =0.50.

1-[(1S,3R)/(1R,3S)-3-(5-Methyl-2-p-tolyloxazol-4-ylmethoxy)cyclohexylmethyl]-1H-indole-2-carboxylic acid

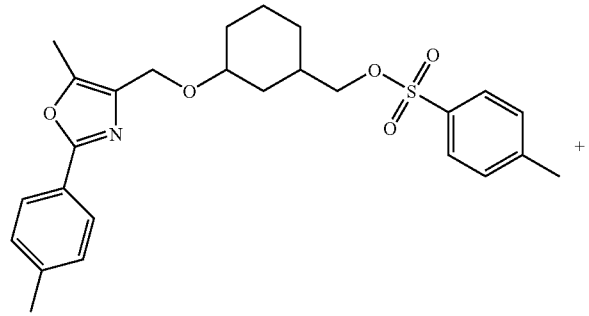

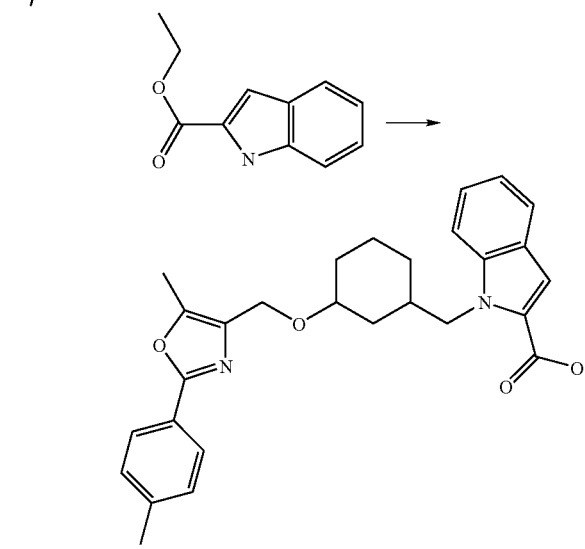

120 mg of ethyl 1H-indole-2-carboxylate are dissolved in 5 ml of dimethylformamide, and 25 mg of sodium hydride (60% strength suspension in mineral oil) are added. After 30 minutes, 100 mg of (1S,3R)/(1R,3S)-3-(5-methyl-2-p-tolyloxazol-4-ylmethoxy)cyclohexylmethyl toluene-4-sulfonate, dissolved in 1 ml of dimethylformamide, are added dropwise. Another 25 mg of sodium hydride (60% strength suspension in mineral oil) are added, and the reaction mixture is warmed at 60° C. for 3 hours. The mixture is diluted by addition of 50 ml of methyl tert-butyl ether and washed three times in each case with 20 ml of water. The organic phase is dried over MgSO4 and the solvent is then removed under reduced pressure. The residue is purified by RP-HPLC. Freeze-drying gives 36 mg of the racemate 1-[(1S,3R)/(1R,3S)-3-(5-methyl-2-p-tolyloxazol-4-ylmethoxy)cyclohexylmethyl]-1H-indole-2-carboxylic acid as a lyophilisate. C28H30N2O4 (458.56), MS (ESI)=459 (M+H$^+$).

Example XXVII

1-[(1S,3R)/(1R,3S)-3-(5-Methyl-2-p-tolyloxazol-4-ylmethoxy)cyclohexylmethyl]-1H-pyrrole-2-carboxylic acid

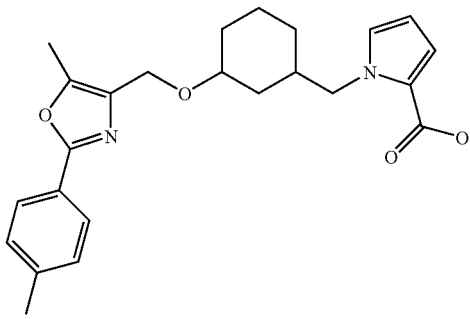

Analogously to Example XXVI, (1S,3R)/(1R,3S)-3-(5-methyl-2-p-tolyloxazol-4-ylmethoxy)cyclohexylmethyl toluene-4-sulfonate and ethyl 1H-pyrrole-2-carboxylate gave the racemate 1-[(1S,3R)/(1R,3S)-3-(5-methyl-2-p-tolyloxazol-4-ylmethoxy)cyclohexylmethyl]-1H-pyrrole-2-carboxylic acid, C24H28N2O4 (408.50), MS (ESI)=409 (M+H$^+$).

Example XXVIII

1-{(1S,3R)/(1R,3S)-3-[2-(3-Methoxyphenyl)-5-methyloxazol-4-ylmethoxy]cyclohexylmethyl}-1H-pyrrole-2-carboxylic acid

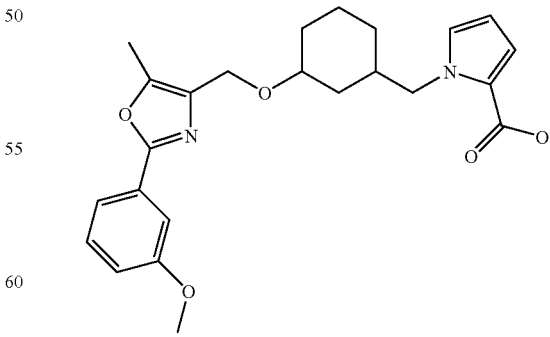

Analogously to Example XXVI, 4-iodomethyl-2-(3-methoxyphenyl)-5-methyloxazole, (1S,3R)/(1R,3S)-3-(tert-butyldiphenylsilanyloxymethyl)cyclohexanol and ethyl 1H-pyrrole-2-carboxylate gave the racemate 1-{(1S,3R)/

(1R,3S)-3-[2-(3-methoxyphenyl)-5-methyloxazol-4-yl-methoxy]cyclohexylmethyl}-1H-pyrrole-2-carboxylic acid, C24H28N2O5 (424.50), MS (ESI)=425 (M+H+).

Example XXIX 1S,3R)/(1R,3S)-3-(5-Methyl-2-p-tolyloxazol-4-yl-methoxy)cyclohexylmethyloxy]thiophen-2-carboxylic acid (1S,3R)/(1R,3S) Methyl 3-(5-methyl-2-p-tolyloxazol-4-ylmethoxy)cyclohexylmethyloxy]thiophene-2-carboxylate

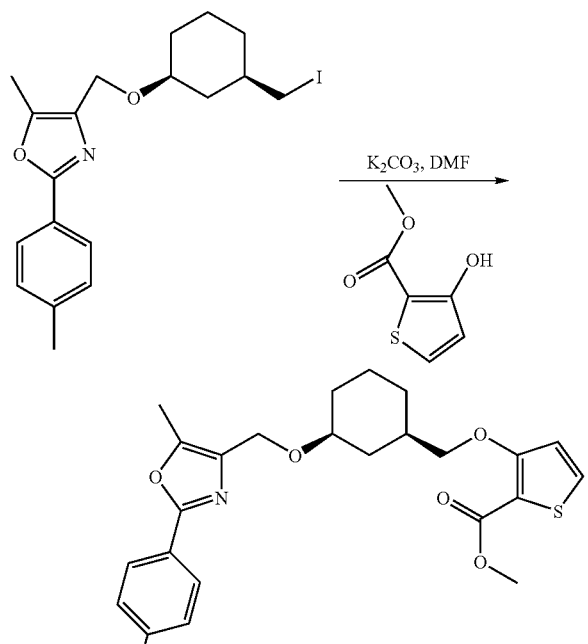

27 mg of methyl 3-hydroxythiophene-2-carboxylate and 67 mg of potassium carbonate are added to 50 mg of 4-((1S,3R)/(1R,3S)-3-iodomethylcyclohexyloxymethyl)-5-methyl-2-p-tolyloxazole in 2 ml of DMF, and the mixture is stirred at 90° C. for 2 h. Water and MTBE are added and the phases are then separated. The organic phase is dried over MgSO₄ and concentrated. Chromatography of the residue on silica gel (heptane/ethyl acetate 5/1) gives 12 mg of the racemate methyl (1S,3R)/(1R,3S)-3-(5-methyl-2-p-tolyloxazol-4-yl-methoxy)cyclohexylmethyloxy]thiophene-2-carboxylate as a yellow oil. C25H29NO5S (455.58); LCMS (ESI): 456.1 (MH+).

(1S,3R)/(1R,3S)-3-(5-Methyl-2-p-tolyloxazol-4-ylmethoxy)cyclohexylmethyloxy]thiophene-2-carboxylic acid

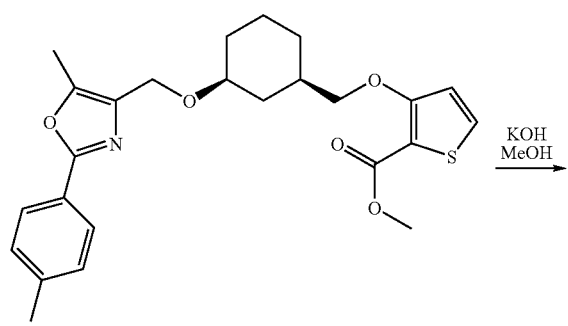

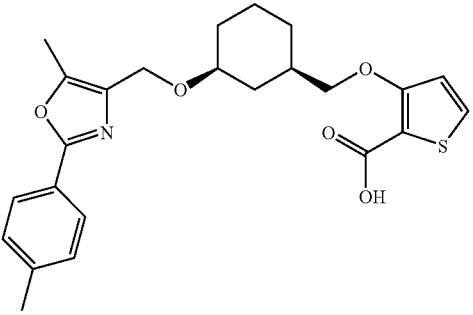

12 mg of methyl (1S,3R)/(1R,3S)-3-(5-methyl-2-p-tolyloxazol-4-ylmethoxy)cyclohexylmethyloxy]thiophene-2-carboxylate are dissolved in 1 ml of methanol, 10 drops of 2N KOH are added and the mixture is stirred at RT for 1 h. 2 ml of saturated NH4Cl solution and MTBE are then added, and the phases are separated. The organic phase is dried over MgSO4 and concentrated, which gives 9.4 mg of (1S,3R)/(1R,3S)-3-(5-methyl-2-p-tolyloxazol-4-ylmethoxy)cyclohexylmethyloxy]thiophene-2-carboxylic acid as a racemate. C24H27NO5S (441.55); LCMS (ESI): 442.1 (MH+).

Example XXX (1S,3R)/(1R,3S)-3-[3-(5-Methyl-2-p-tolyloxazol-4-ylmethoxy)cyclohexylmethoxy]-5-trifluoromethylthiophene-2-carboxylic acid

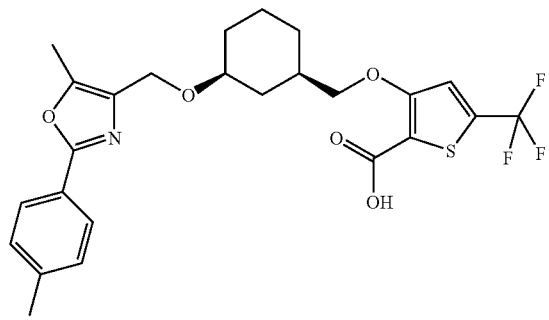

Analogously to Example XXIX, 4-((1S,3R)/(1R,3S)-3-iodomethylcyclohexyloxymethyl)-5-methyl-2-p-tolyloxazole and methyl 3-hydroxy-5-trifluoromethylthiophene-3-carboxylate give (1S,3R)/(1R,3S)-3-[3-(5-methyl-2-p-tolyloxazol-4-ylmethoxy)cyclohexylmethoxy]-5-trifluoromethylthiophene-2-carboxylic acid as a racemate. C25H26F3NO5S (509.55), LCMS (ESI)=510.1 (MH+).

Example XXXI

6-Chloro-3-[1S,3R)/(1R,3S)-3-(5-methyl-2-p-tolyloxazol-4-ylmethoxy)cyclohexylmethoxy]benzo[b]thiophene-2-carboxylic acid

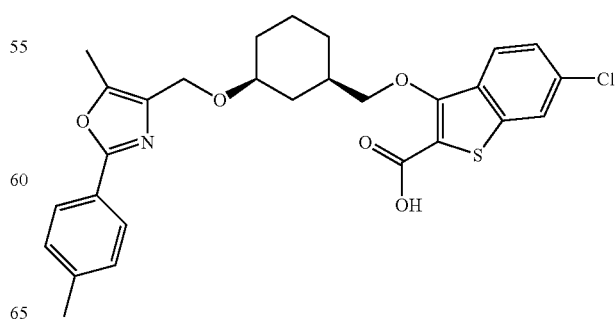

Analogously to Example XXIX, 4-((1S,3R/(1R,3S)-3-iodomethylcyclohexyloxymethyl)-5-methyl-2-p-tolyloxazoleand methyl 6-chloro-3-hydroxybenzo[b]thiophene-2-carboxylate give 6-chloro-3-[(1S,3R)/(1R,3S)-3-(5-methyl-2-p-tolyloxazol-4-ylmethoxy)cyclohexylmethoxy]benzo[b]thiophene-2-carboxylic acid as a racemate. C28H28ClNO5S (526.06), LCMS (ESI): 526.1 (MH+).

We claim:

1. A compound of the formula I

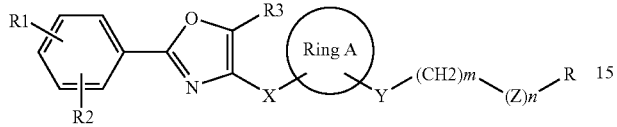

wherein
ring A is cyclohexandiyl;
R1, R2 are each independently H, F, Br, Cl, $SF_5$, S—($C_1$-$C_6$)-alkyl, $CF_3$, $OCF_3$, ($C_1$-$C_6$)-alkyl, O—($C_1$-$C_6$)-alkyl, $SCF_3$, phenoxy, $OCF_2CHF_2$, $OCF_2CF_3$, ($C_1$-$C_6$)-alkyl-($C_1$-$C_6$)-alkoxy, O($C_1$-$C_6$)-alkyl-($C_1$-$C_6$)-alkoxy or benzyloxy;
R3 is H, $CF_3$, ($C_1$-$C_6$)-alkyl, ($C_3$-$C_8$)-cycloalkyl or phenyl;
X is ($C_1$-$C_6$)-alkanediyl, wherein one or more carbon atoms therein are optionally replaced by oxygen atoms;
Y is S, O or a bond;
m is 1, 2 or 3;
n is 0 or 1;
Z is O, S, CO or CO—NH;
R is H, OH, $CH_2$—CO—NH—OH, $CH_2$—CO—NH—($C_1$-$C_6$)-alkyl, $CH_2$—CO—NH—($C_1$-$C_6$)-alkoxy, NR4R5 or a 5-, 6-, 7-, 8-, 9-, 10-, 11- or 12-membered mono or bicyclic ring that is unsaturated, partially unsaturated or saturated, and optionally contains one to four heteroatoms selected from the group consisting of N, O and S, and wherein said 5-, 6-, 7-, 8-, 9-, 10-, 11- or 12-membered mono or bicyclic ring is optionally benzo-fused, and optionally substituted by F, Cl, Br, CN, SH, COOH, ($C_1C_4$)-alkyl, ($C_1$-$C_6$)-alkoxy, $SO_2$—($C_1$-$C_4$)-alkyl, $NO_2$, $CF_3$, $OCF_3$, ($C_1$-$C_6$)-alkyl-($C_1$-$C_6$)-alkoxy, ($C_1$-$C_6$)-alkoxy-($C_1$-$C_6$)-alkoxy, ($C_1$-$C_6$)-alkoxy-phenyl, phenoxy, $NHSO_2CF_3$ or $B(OH)_2$;
R4 is H or ($C_1$-$C_6$)-alkyl;
R5 is OH, $NH_2$, $SO_2$—$CF_3$, $SO_2$-phenyl-$CF_3$, CO—$CF_3$, ($C_1$-$C_6$)-alkoxy or phenyl optionally substituted by $CH_3$ or COOH; or
R4 and R5, taken together with the nitrogen atom to which they are attached, form a 5-membered aromatic heterocycle which is optionally fused to an aromatic 5-, 6-, or 7-membered ring, said aromatic 5-, 6-, or 7-membered ring optionally having one, two, three or four nitrogen atoms, and optionally substituted by F, Cl, Br, $CF_3$, $OCF_3$, COOH, $SO_2CH_3$, CN, ($C_1$-$C_4$)-alkoxy, ($C_1$-$C_4$)-alkyl, ($C_1$-$C_6$)-alkyl-phenyl, ($C_1$-$C_6$)-alkyl-($C_1$-$C_6$)-alkoxy, ($C_1$-$C_6$)-alkoxy-($C_1$-$C_6$)-alkoxy, ($C_1$-$C_6$)-alkoxy-phenyl or phenoxy;
and pharmaceutically acceptable salts thereof.

2. The compound of claim 1 wherein:
ring A is cyclohexandiyl, and
X is ($C_1$-$C_6$)-alkanediyl, wherein one carbon atom is optionally replaced by an oxygen atom.

3. The compound of claim 2 wherein:
ring A is cyclohexane-1,3-diyl; and
X is $CH_2$—O.

4. The compound of claim 3 wherein:
ring A is cyclohexane-1,3-diyl;
X is $CH_2$—O; and
Y is O.

5. The compound of claim 4 wherein said cyclohexane-1,3-diyl ring is attached cis.

6. The compound of claim 5 wherein:
R1/R2 are each independently H, ($C_1$-$C_4$)-alkyl or ($C_1$-$C_4$)-alkoxy; and
R3 is ($C_1$-$C_4$)-alkyl.

7. The compound of claim 6 wherein:
Y is O;
m is 3; and
n is 0.

8. The compound of claim 6 wherein:
Y is O;
m is 2; and
n is 0.

9. The compound of claim 6 wherein:
Y is O;
m is 2;
n is 1; and
Z is O.

10. The compound of claim 6 wherein:
Y is O;
m is 1; and
n is 0.

11. The compound of claim 6 wherein:
Y is a bond;
in is 1; and
n is 0.

12. The compound of claim 6 wherein:
Y is a bond;
m is 1;
n is 1; and
Z is O.

13. The compound of claim 7 wherein:
Y is O;
m is 3;
n is 0; and
R is tetrazole or $NHSO_2CF_3$.

14. The compound of claim 8 wherein:
Y is O;
m is 2;
n is 0; and
R is tetrazole, $NHSO_2CF_3$ or NR4R5 denoting indole or 6-azaindole and wherein said indole and 6-azaindole groups are optionally substituted by F, Br, CN, COOH, ($C_1C_4$)-alkyl, ($C_1$-$C_4$)-alkoxy, $SO_2$—$CH_3$, ($C_1$-$C_6$)-alkoxy-($C_1$-$C_6$)-alkoxy or benzoxy.

15. The compound of claim 9 wherein:
Y is O;
m is 2;
n is 1;
Z is O; and
R is phenyl or thiophene, each of which is optionally substituted by F, COOH, ($C_1$-$C_4$)-alkyl, ($C_1$-$C_4$)-alkoxy, $NO_2$, $CF_3$, benzyloxy or $B(OH)_2$.

16. The compound of claim 10 wherein:
Y is O;
m is 1;
n is 0; and
R is phenyl optionally substituted with $NHSO_2CF_3$ or $B(OH)_2$.

17. The compound of claim 11 wherein:
Y is a bond;
m is 1;
n is 0; and
R is NR4R5 denoting pyrrole or indole, both of which are substituted by COOH.

18. The compound of claim 12 wherein:
Y is a bond;
m is 1;
n is 1;
Z is O; and
R is thiophene or benzothiophene, each of which is optionally substituted by COOH, Cl or $CF_3$.

19. A pharmaceutical composition comprising a pharmaceutically acceptable carrier and one or more compounds of claim 1.

20. A method of treating disorders of fatty acid metabolism and glucose utilization comprising administering to a patient in need thereof a therapeutically effective amount of a compound of claim 1.

21. A method of treating disorders of insulin resistance comprising administering to a patient in need thereof a therapeutically effective amount of a compound of claim 1.

22. A method of treating diabetes mellitus including the prevention of the squelae associated therewith comprising administering to a patient in need thereof a therapeutically effective amount of a compound of claim 1.

23. A method of treating dyslipidemia and squelae associated therewith comprising administering to a patient in need thereof a therapeutically effective amount of a compound of claim 1.

24. A method of treating metabolic syndrome and conditions associated therewith comprising administering to a patient in need thereof a therapeutically effective amount of a compound of claim 1.

25. A method of treating disorders of fatty acid metabolism and glucose utilization comprising administering to a patient in need thereof a therapeutically effective amount of a compound of claim 1 in combination with at least one further active compound.

26. A method of treating disorders of insulin resistance comprising administering to a patient in need thereof a therapeutically effective amount of a compound of claim 1 in combination with at least one further active compound selected from antidiabetics, lipid modulators, antiobesity agents and medicaments having an anti-inflammatory effect.

* * * * *